United States Patent
Chen et al.

(10) Patent No.: US 8,765,968 B2
(45) Date of Patent: Jul. 1, 2014

(54) POLYMERIC SEMICONDUCTORS, DEVICES, AND RELATED METHODS

(75) Inventors: Zhikuan Chen, Singapore (SG); Jun Li, Singapore (SG); Beng Ong, Singapore (SG); Samarendra P. Singh, Singapore (SG); Hoi Kai Ivy Wong, Singapore (SG); Kok Haw Ong, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 13/393,218

(22) PCT Filed: Apr. 30, 2010

(86) PCT No.: PCT/SG2010/000172
§ 371 (c)(1),
(2), (4) Date: Feb. 28, 2012

(87) PCT Pub. No.: WO2011/025453
PCT Pub. Date: Mar. 3, 2011

(65) Prior Publication Data
US 2012/0156829 A1    Jun. 21, 2012

Related U.S. Application Data

(60) Provisional application No. 61/272,182, filed on Aug. 28, 2009.

(30) Foreign Application Priority Data

Oct. 22, 2009    (WO) ................ PCT/SG2009/000393

(51) Int. Cl.
C08G 61/12    (2006.01)
C07D 409/14    (2006.01)
C07D 417/00    (2006.01)
H01B 1/12    (2006.01)
H01L 51/30    (2006.01)
H01L 51/40    (2006.01)

(52) U.S. Cl.
USPC ...... 548/139; 438/99; 257/E51.029; 136/263; 528/380; 549/50

(58) Field of Classification Search
CPC ............. H01I 51/0558; H01I 51/0545; H01I 51/0036; C07D 285/02; C07D 333/10; C07D 417/14; C08G 2261/3228; C08G 2261/3246
USPC ................ 438/99; 257/E51.024, E51.029; 136/263; 548/126, 139; 549/50; 528/373, 377, 380
See application file for complete search history.

(56) References Cited

U.S. PATENT DOCUMENTS

| | | | |
|---|---|---|---|
| 6,791,129 B2 | 9/2004 | Inukai | |
| 7,112,679 B2 | 9/2006 | Zhou et al. | |
| 7,132,500 B2 | 11/2006 | Ong et al. | |
| 7,132,682 B2 | 11/2006 | Ong et al. | |
| 7,141,644 B2 | 11/2006 | Ong et al. | |
| 7,223,484 B2 | 5/2007 | Stössel et al. | |
| 7,244,809 B2 | 7/2007 | Giles et al. | |
| 7,282,733 B2 | 10/2007 | Ong et al. | |
| 7,294,288 B2 | 11/2007 | Koller et al. | |
| 7,368,510 B2 | 5/2008 | Lee et al. | |
| 7,517,945 B2 | 4/2009 | Ong et al. | |
| 8,329,915 B2 * | 12/2012 | Moawia et al. | 548/126 |
| 8,624,232 B2 | 1/2014 | Sonar et al. | |
| 2003/0186079 A1 * | 10/2003 | Towns et al. | 428/690 |
| 2005/0082525 A1 | 4/2005 | Heeney et al. | |
| 2006/0081839 A1 | 4/2006 | Jeong et al. | |
| 2006/0113527 A1 | 6/2006 | Han et al. | |
| 2007/0090371 A1 | 4/2007 | Drechsel et al. | |
| 2007/0228359 A1 | 10/2007 | Helm et al. | |
| 2008/0197768 A1 * | 8/2008 | Conway et al. | 313/504 |
| 2008/0315187 A1 | 12/2008 | Bazan et al. | |
| 2009/0032106 A1 | 2/2009 | Sellinger et al. | |
| 2009/0032808 A1 | 2/2009 | Bazan et al. | |
| 2009/0065766 A1 | 3/2009 | Li | |
| 2009/0065878 A1 | 3/2009 | Li | |
| 2009/0171048 A1 | 7/2009 | Chan et al. | |
| 2010/0006154 A1 | 1/2010 | Kitazawa et al. | |
| 2010/0327273 A1 * | 12/2010 | Li et al. | 257/40 |
| 2010/0331550 A1 * | 12/2010 | Moawia et al. | 548/126 |

U.S. PATENT DOCUMENTS

| | | | |
|---|---|---|---|
| 2011/0023964 A1* | 2/2011 | Kitazawa et al. | 136/263 |
| 2011/0121273 A1* | 5/2011 | Jo et al. | 257/40 |
| 2011/0156018 A1 | 6/2011 | Moriwaki et al. | |
| 2011/0201777 A1 | 8/2011 | Kondou et al. | |
| 2012/0156829 A1* | 6/2012 | Chen et al. | 438/99 |

FOREIGN PATENT DOCUMENTS

| | | | |
|---|---|---|---|
| CA | 2 625 306 | * 9/2009 | H01L 51/30 |
| EP | 2 033 983 A2 | 3/2009 | |
| EP | 2 034 537 A2 | 3/2009 | |
| EP | 2 327 734 A1 | 6/2011 | |
| EP | 2 338 925 A1 | 6/2011 | |
| JP | 2001-515933 | 9/2001 | |
| JP | 2008-266459 | 11/2008 | |
| JP | 2009-155648 | 7/2009 | |
| JP | 2009-158921 A | 7/2009 | |
| JP | 2009-267196 | * 11/2009 | H01L 51/42 |
| JP | 2010-018790 | 1/2010 | |
| JP | 2010-520322 | 10/2010 | |
| WO | WO 99/12989 A1 | 3/1999 | |
| WO | WO 2005/049695 A1 | 6/2005 | |
| WO | WO 2005/073265 A1 | 8/2005 | |
| WO | WO 2007/136351 A1 | 11/2007 | |
| WO | WO 2008/000664 A1 | 1/2008 | |
| WO | WO 2008/044585 A1 | 4/2008 | |
| WO | WO 2008/166019 A2 | 9/2008 | |
| WO | WO 2008/127029 A1 | 10/2008 | |
| WO | WO 2009/105041 | * 8/2009 | H01L 51/30 |
| WO | WO 2009/105041 A1 | 8/2009 | |
| WO | WO 2009/105042 | * 8/2009 | H01L 51/30 |
| WO | WO 2009/105042 A1 | 8/2009 | |
| WO | WO 2009-125647 | * 10/2009 | H01L 51/30 |
| WO | WO 2009/139339 A1 | 11/2009 | |
| WO | WO 2010/026972 A1 | 3/2010 | |
| WO | WO 2010/036494 A1 | 4/2010 | |
| WO | WO 2010/044470 A1 | 4/2010 | |
| WO | WO 2010/096019 A1 | 8/2010 | |

OTHER PUBLICATIONS

Melucci et al., Liquid-Crystalline Rigid-Core Semiconductor Oligothiophenes: Influence of Molecular Structure on Phase Behavior and Thin-Film Properties, Chem. Eur. J. 2007, 13, pp. 100046-10054.*

Liang et al., Design and Synthesis of Alternating Regioregular Oligthiophenes/Benzothiadiazole Copolymers for Organic Solar Cells, Macromolecules, 2009, 42, pp. 6107-6114.*

Yue et al., Poly(oligothiophene-alt-benzothiadiazole)s: Tuning the Structures of Oligothiophene Units toward a High-Mobility "Black" Conjugated Polymers, Macromolecules 2009, 42, pp. 6510-6518.*

Bundgaard et al., Low band gap polymers for organic solar cells, Proc. of SPIE, vol. 6334, 2006, pp. 63340T-1 to 63340T-10.*

Bundgaard et al., Low-Band-Gap Conjugated Polymers Based on Thiopene, Benzothiadiazole, and Benzobis(thiadiazole), Macromolecules, 2006, 39, pp. 2823-2831.*

Bundgaard et al., Bulk heterojunctions based on a low band gap copolymer of thiopene and benzothiadiazole, Solar Energy Materials & Solar Cells, 91 (2007), pp. 1631-1637.*

Bernède, J. C., "Organic Photovoltaic Cells: History, Principle and Techniques", Journal of the Chilean Chemical Society, vol. 53, No. 3, pp. 1549-1564, (2008).

Biniek, Laure, et al., "A [3,2-b]thienothiophene-alt-benzothiadiazole Copolymer for Photovoltaic Applications: Design, Synthesis, Material Characterization and Device Performances", Journal of Materials Chemistry, vol. 19, pp. 4946-4951, (2009).

Blom, Paul W. M., et al., "Device Physics of Polymer:Fullerene Bulk Heterojunction Solar Cells", Advanced Materials, vol. 19, pp. 1551-1566, (2007).

Blouin, Nicolas, et al., "A Low-Bandgap Poly(2,7-Carbazole) Derivative for Use in High-Performance Solar Cells", Advanced Materials, vol. 19, pp. 2295-2300, (2007).

Bundgaard, Eva, et al., "Low Band Gap Polymers for Organic Photovoltaics", Solar Energy Materials & Solar Cells, vol. 91, pp. 954-985, (2007).

Cha, Soon Wook, et al., "Electroluminescence of LEDs consisting Two Layers of $Alq_3$ and High $T_g$, Blue-Light Emitting Branched Compounds", Synthetic Metals, vol. 143, pp. 97-101, (2004).

Chan, Hardy Sze On, et al., "Synthesis, Characterization and Applications of Thiophene-Based Functional Polymers", Progress in Polymer Science, vol. 23, pp. 1167-1231, (1998).

Chen, Chih-Ping, et al., "Low-Bandgap Poly(Thiophene-Phenylene-Thiophene) Derivatives with Broaden Absorption Spectra for Use in High-Performance Bulk-Heterojunction Polymer Solar Cells", Journal of the American Chemical Society, vol. 130, pp. 12828-12833, (2008).

Chen, Hsiang-Yu, et al., "Polymer Solar Cells with Enhanced Open-Circuit Voltage and Efficiency", Nature Photonics, vol. 3, pp. 649-653, (Nov. 2009).

Frey, Joseph, et al., "Improved Synthesis of dithieno[3,2-b:2',3'-d]thiophene (DTT) and Derivatives for Cross Coupling", Chemical Communications, vol. 20, pp. 2424-2425, (2002).

Gong, Cheng, et al., "Polymer Solar Cell based on poly(2,6-bis(3-alkylthiophen-2-yl)dithieno-[3,2-b;2',3'-d]thiophene)", Solar Energy Materials & Solar Cells, vol. 93, pp. 1928-1931, (2009).

Greenham, N. C., et al., "Efficient Light Emitting Diodes based on Polymers with High Electron Affinities", Nature, vol. 365, pp. 628-630, (Oct. 14, 1993).

Günes, Serap, et al., "Conjugated Polymer-Based Organic Solar Cells", Chemical Reviews, vol. 107, No. 4, pp. 1324-1338, (2007).

Hou, Jianhui, et al., "Synthesis, Characterization, and Photovoltaic Properties of a Low Band Gap Polymer Based on Silole-Containing Polythiophenes and 2,1,3-Benzothiadiazole", Journal of the American Chemical Society, vol. 130, No. 48, pp. 16144-16145, (2008).

Hughes, Gregory, et al., "Electron-Transporting Materials for Organic Electroluminescent and Electrophosphorescent Devices", Journal of Materials Chemistry, vol. 15, pp. 94-107, (2005).

PCT International Search Report and Written Opinion of the International Searching Authority issued in PCT Application No. PCT/SG2009/000393, 10 pages, (Dec. 24, 2009).

PCT International Preliminary Report on Patentability issued in PCT Application No. PCT/SG2009/000393, 4 pages, (Sep. 27, 2011).

PCT International Search Report and Written Opinion of the International Searching Authority issued in PCT Application No. PCT/SG2010/000172, 13 pages, (Jul. 29, 2010).

PCT International Preliminary Report on Patentability issued in PCT Application No. PCT/SG2010/000172, 4 pages, (Jul. 25, 2011).

PCT International Search Report and Written Opinion of the International Searching Authority issued in PCT Application No. PCT/SG2010/000174, 11 pages, (Jul. 12, 2010).

PCT Written Opinion of the International Preliminary Examining Authority issued in PCT Application No. PCT/SG2010/000174, 5 pages, (Aug. 26, 2011).

PCT Notification of Transmittal of International Preliminary Report on Patentability (Chapter II of the Patent Cooperation Treaty) issued in PCT Application No. PCT/SG2010/000174, 6 pages, (Dec. 7, 2011).

PCT International Search Report and Written Opinion of the International Searching Authority issued in PCT Application No. PCT/SG2010/000175, 6 pages, (Jul. 12, 2010).

PCT International Preliminary Report on Patentability (Chapter I of the Patent Cooperation Treaty) issued in PCT Application No. PCT/SG2010/000175, 4 pages, (Feb. 28, 2012).

Katz, Howard E., et al., "Synthetic Chemistry for Ultrapure, Processable, and High-Mobility Organic Transistor Semiconductors", Accounts of Chemical Research, vol. 34, No. 5, pp. 359-369, (2001).

Kietzke, Thomas, et al., "Efficient Polymer Solar Cells Based on M3EH-PPV", Chemistry of Materials, vol. 17, No. 26, pp. 6532-6537, (2005).

Kietzke, Thomas, et al., "Effect of Annealing on the Characteristics of Organic Solar Cells: Polymer Blends with a 2-Vinyl-4,5-dicyanoimidazole Derivative", Macromolecules, vol. 40, No. 13, pp. 4424-4428, (2007).

Kim, Bong Soo, et al., "Charge Mobilities and Luminescence Characteristics of Blue-Light Emitting Bent Carbazole Trimers Connected through Vinylene Linkers—Effect of Nitrile Substituents", Synthetic Metals, vol. 145, pp. 229-235, (2004).

(56) References Cited

OTHER PUBLICATIONS

Kim, Felix Sunjoo, et al., "High-Mobility Ambipolar Transistors and High-Gain Inverters from a Donor-Acceptor Copolymer Semiconductor", Advanced Materials, vol. 22, pp. 478-482, (2010).
Kim, Sun Woong, et al., "2.4-in. Monochrome Small Molecular OLED Display for Mobile Application", Current Applied Physics, vol. 2, pp. 335-338, (2002).
Kitamura, Chitoshi, et al., "Synthesis and Properties of a New Ethyne-Linked Donor/Acceptor Pentamer", Tetrahedron Letters, vol. 43, pp. 3373-3376, (2002).
Kroon, Renee, et al., "Small Bandgap Polymers for Organic Solar Cells (Polymer Material Development in the Last 5 Years)", Polymer Reviews, vol. 48, pp. 531-582, (2008).
Kulkarni, Abhishek P., et al., "Electron Transport Materials for Organic Light-Emitting Diodes", Chemistry of Materials, vol. 16, No. 23, pp. 4556-4573, (2004).
Li, Jun, et al., "High-Performance Thin-Film Transistors from Solution-Processed Dithienothiophene Polymer Semiconductor Nanoparticles", Chemistry of Materials, vol. 20, No. 6, pp. 2057-2059, (Mar. 25, 2008).
Li, Ji-Cheng, et al., "Synthesis and Characterization of a Thiophene-Benzothiadiazole Copolymer", Macromolecular Research, vol. 17, No. 5, pp. 356-360, (2009).
Li, Yuning, et al., "Poly(2,5-bis(2-thienyl)-3,6-dialkylthieno[3,2-b]thiophene)s—High-Mobility Semiconductors for Thin-Film Transistors", Advanced Materials, vol. 18, pp. 3029-3032, (2006).
Li, Yongfang, et al., "Conjugated Polymer Photovoltaic Materials with Broad Absorption Band and High Charge Carrier Mobility", Advanced Materials, vol. 20, pp. 2952-2958, (2008).
Liang, Fushun, et al., "Design and Synthesis of Alternating Regioregular Oligothiophenes/Benzothiadiazole Copolymers for Organic Solar Cells", Macromolecules, vol. 42, No. 16, pp. 6107-6114, (2009).
Liang, Yongye, et al., "Development of New Semiconducting Polymers for High Performance Solar Cells", Journal of the American Chemical Society, vol. 131, No. 1, pp. 56-57, (2009).
Lloyd, Matthew T., et al., "Photovoltaics from Soluble Small Molecules", Materials Today, vol. 10, No. 11, pp. 34-41, (Nov. 2007).
Lu, Jianping, et al., "Crystalline Low Band-Gap Alternating Indolocarbazole and Benzothiadiazole-Cored Oligothiophene Copolymer for Organic Solar Cell Applications", Chemical Communications, pp. 5315-5317, (2008).
Ma, Wanli, et al., "Thermally Stable, Efficient Polymer Solar Cells with Nanoscale Control of the Interpenetrating Network Morphology", Advanced Functional Materials, vol. 15, pp. 1617-1622, (2005).
Mayer, Alex C., et al., "Polymer-Based Solar Cells", Materials Today, vol. 10, No. 11, pp. 28-33, (Nov. 2007).
McCulloch, Iain, et al., "Liquid-Crystalline Semiconducting Polymers with High Charge-Carrier Mobility", Nature Materials, vol. 5, pp. 328-333, (Apr. 2006).
Meier, Herbert, et al., "The Effect of 2,2-dicyanovinyl Groups as Electron Acceptors in Push-Pull Substituted oligo(1,4-phenylenevinylene)s", Tetrahedron Letters, vol. 44, pp. 1915-1918, (2003).
Meier, Herbert, "Conjugated Oligomers with Terminal Donor-Acceptor Substitution", Angewandte Chemie International Edition, vol. 44, pp. 2482-2506, (2005).
Mühlbacher, David, et al., "High Photovoltaic Performance of a Low-Bandgap Polymer", Advanced Materials, vol. 18, pp. 2884-2889, (2006).
Ong, Beng S., et al., "High-Performance Semiconducting Polythiophenes for Organic Thin-Film Transistors", Journal of the American Chemical Society, vol. 126, No. 11, pp. 3378-3379, (2004).
Ooi, Zi En, et al., "Solution Processable Bulk-Heterojunction Solar Cells using a Small Molecule Acceptor", Journal of Materials Chemistry, vol. 18, pp. 4619-4622, (2008).
Pan, Hualong, et al., "Benzodithiophene Copolymer—A Low-Temperature, Solution-Processed High-Performance Semiconductor for Thin-Film Transistors", Advanced Functional Materials, vol. 17, pp. 3574-3579, (2007).
Pan, Hualong, et al., "Low-Temperature, Solution-Processed, High-Mobility Polymer Semiconductors for Thin-Film Transistors", Journal of the American Chemical Society, vol. 129, No. 14, pp. 4112-4113, (2007).
Peet, J., et al., "Efficiency Enhancement in Low-Bandgap Polymer Solar Cells by Processing with Alkane Dithiols", Nature Materials, vol. 6, pp. 497-500, (Jul. 2007).
Salleo, A., et al., "Polymer Thin-Film Transistors with Chemically Modified Dielectric Interfaces", Applied Physics Letters, vol. 81, No. 23, pp. 4383-4385, (Dec. 2, 2002).
Shin, Richard Yee Cheong, et al., "N-Type Conjugated Materials Based on 2-Vinyl-4,5-dicyanoimidazoles and Their Use in Solar Cells", Chemistry of Materials, vol. 19, No. 8, pp. 1892-1894, (2007).
Shin, Richard Y. C., et al., "Electron-Accepting Conjugated Materials Based on 2-Vinyl-4,5-dicyanoimidazoles for Application in Organic Electronics", Journal of Organic Chemistry, vol. 74, No. 9, pp. 3293-3298, (2009).
Sirringhaus, Henning, et al., "Integrated Optoelectronic Devices Based on Conjugated Polymers", Science, vol. 280, pp. 1741-1744, (Jun. 12, 1998).
Sirringhaus, H., et al., "Two-Dimensional Charge Transport in Self-Organized, High-Mobility Conjugated Polymers", Nature, vol. 401, pp. 685-688, (Oct. 14, 1999).
Slooff, L. H., et al., "Determining the Internal Quantum Efficiency of Highly Efficient Polymer Solar Cells through Optical Modeling", Applied Physics Letters, vol. 90, Article 143506, 4 pages, (2007).
Subbiah, Jegadesan, et al., "Efficient Green Solar Cells via a Chemically Polymerizable Donor-Acceptor Heterocyclic Pentamer", ACS Applied Materials & Interfaces, vol. 1, No. 6, pp. 1154-1158, (2009).
Takahashi, Masabumi, et al., "Palladium-Catalyzed C—H Homocoupling of Bromothiophene Derivatives and Synthetic Application to Well-Defined Oligothiophenes", Journal of the American Chemical Society, vol. 128, No. 33, pp. 10930-10933, (2006).
Tamayo, Arnold B., et al., "A Low Band Gap, Solution Processable Oligothiophene with a Diketopyrrolopyrrole Core for Use in Organic Solar Cells", Journal of Physical Chemistry C, vol. 112, No. 30, pp. 11545-11551, (2008).
Thelakkat, Mukundan, "Star-Shaped, Dendrimeric and Polymeric Triarylamines as Photoconductors and Hole Transport Materials for Electro-Optical Applications", Macromolecular Materials and Engineering, vol. 287, No. 7, pp. 442-461, (2002).
Wang, Ergang, et al., "High-Performance Polymer Heterojunction Solar Cells of a Polysilafluorene Derivative", Applied Physics Letters, vol. 92, Article 033307, 4 pages, (2008).
Wienk, Martijn M., et al., "Narrow-Bandgap Diketo-Pyrrolo-Pyrrole Polymer Solar Cells: The Effect of Processing on the Performance", Advanced Materials, vol. 20, pp. 2556-2560, (2008).
Winder, Christoph, et al., "Low Bandgap Polymers for Photon Harvesting in Bulk Heterojunction Solar Cells", Journal of Materials Chemistry, vol. 14, pp. 1077-1086, (2004).
Wong, Henry M. P., et al., "Donor and Acceptor Behavior in a Polyfluorene for Photovoltaics", Journal of Physical Chemistry C, vol. 111, No. 13, pp. 5244-5249, (2007).
Wong, Man Shing, et al., "Synthesis and Functional Properties of Donor-Acceptor π-Conjugated Oligomers", Chemistry of Materials, vol. 15, No. 5, pp. 1198-1203, (2003).
Yu, Chao-Ying, et al., "Thiophene/Phenylene/Thiophene-Based Low-Bandgap Conjugated Polymers for Efficient Near-Infrared Photovoltaic Applications", Chemistry of Materials, vol. 21, pp. 3262-3269, (2009).
Yue, Wei, et al., "Poly(oligothiophene-alt-benzothiadiazole)s: Tuning the Structures of Oligothiophene Units toward High-Mobility "Black" Conjugated Polymers", Macromolecules, vol. 42, No. 17, pp. 6510-6518, (2009).
Zhang, Xin, et al., "Donor/Acceptor Vinyl Monomers and their Polymers: Synthesis, Photochemical and Photophysical Behaviour", Progress in Polymer Science, vol. 31, pp. 893-948, (2006).

(56) References Cited

OTHER PUBLICATIONS

Zhang, Shiming, et al., "Synthesis of a Soluble Conjugated Copolymer based on Dialkyl-Substituted Dithienothiophene and its Application in Photovoitaic Cells", Polymer, vol. 50, pp. 3595-3599, (2009).
Zhang, Shiming, et al., "Low Bandgap π-Conjugated Copolymers based on Fused Thiophenes and Benzothiadiazole: Synthesis and Structure-Property Relationship Study", Journal of Polymer Science, Part A: Polymer Chemistry, vol. 47, pp. 5498-5508, (2009).
Zhu, Y. et al., "Highly Luminescent 1,4-Diketo-3,6-diphenylpyrrolo[3,4-c]pyrrole- (DPP-) Based Conjugated Polymers Prepared Upon Suzuki Coupling", Macromolecules, vol. 40, No. 19, pp. 6981-6989, (2007).
Zhu, Zhengguo, et al., "Panchromatic Conjugated Polymers Containing Alternating Donor/Acceptor Units for Photovoltaic Applications", Macromolecules, vol. 40, No. 6, pp. 1981-1986, (2007).
Zou, Yingping, et al., "A High-Mobility Low-Bandgap Poly(2,7-carbazole) Derivative for Photovoltaic Applications", Macromolecules, vol. 42, No. 8, pp. 2891-2894, (2009).
First Office Action for corresponding Chinese Patent Application No. 201080041373.3, 13 pages, (Apr. 28, 2013).
1st Office ACtion Issued in Chinese Patent Application No. 201080041373.3 dated Apr. 28, 2013.
Zhang, S. et al. "Synthesis of a soluble conjugated copolymer based on dialkyl-substituted dithienothiophene and its application in photovoltaic cells." Polymer 50 (2009) 3595-3599.
Response to PCT Written Opinion mailed Jul. 12, 2010 and PCT Demand for PCT Application No. PCT/SG2010/000174, 50 pgs., (Jun. 28, 2011).
Response to PCT Written Opinion mailed Aug. 26, 2011 for PCT Application No. PCT/SG2010/000174. 33 pgs., (Oct. 25, 2011).
PCT Notification concerning Transmittal of International Preliminary Report on Patentability (Chapter I of the Patent Cooperation Treaty) for PCT Application No. PCT/SG2010/000175, 5 pgs., (Mar. 8, 2012).
Office Action for Japanese Counterpart Patent Application No. 2012-526691 with full English translation, 8 pgs. (Nov. 6. 2013).
Extended European Search Report for EP Counterpart Patent Application No. 10812410.Aug. 1302, 12 pgs. (Jan. 7, 2014).
Mingqian He et al., "Structure vs. Property Relationship in High Mobility Fused Thiophene Polymers," Proc. Of SPIE, vol. 7417, pp. 74170F-1 to 74170E-11 (Aug. 2009).

\* cited by examiner

*Primary Examiner* — Mary Wilczewski
(74) *Attorney, Agent, or Firm* — Blakely, Sokoloff, Taylor & Zafman LLP

(57) ABSTRACT

A polymer comprises a polymeric chain represented by formula (I) or (II). In formula (I), a, b, c, d, and n are integers, a from 0 to 3, b from 1 to 5, c from 1 to 3, d from 1 to 5, and n from 2 to 5000; $R^1$ and $R^2$ are side chains; $R^3$ and $R^4$ are each independently H or a side chain; and when a is 0, $R^3$ and $R^4$ are side chains. In formula (II), a, b, c, d, e, and n are integers, a from 1 to 3, b and c being independently 0 or 1, d and e being independently 1 or 2, and n from 2 to 5000; $R^1$ and $R^2$ are side chains except —COOalkyl; and $X^1$, $X^2$ and $X^3$ are independently O, S, or Se. Semiconductors and devices comprising the polymer are also provided.

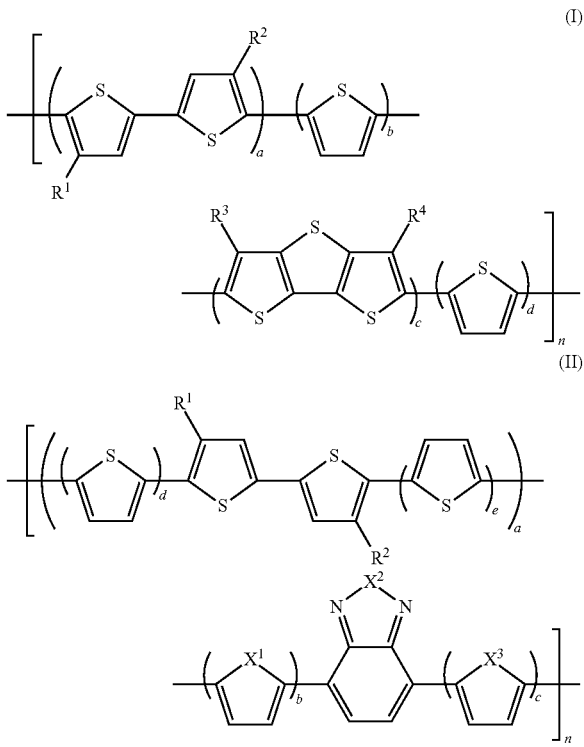

9 Claims, 13 Drawing Sheets

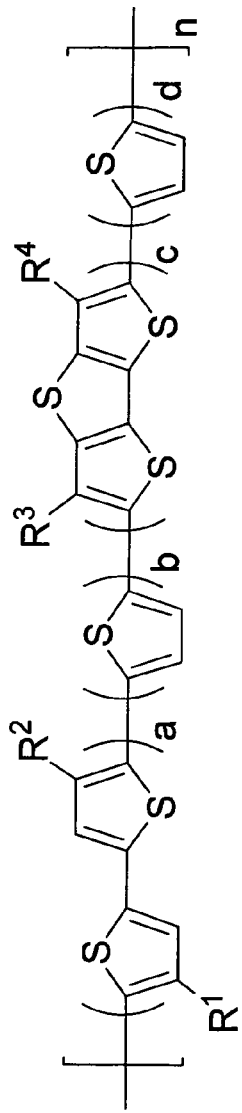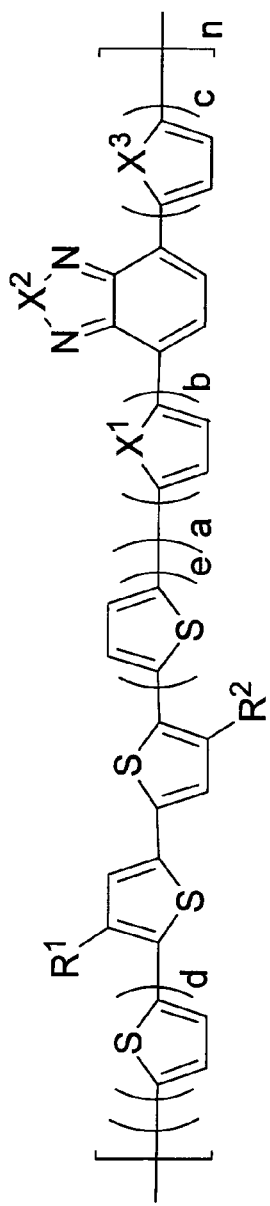
FIG. 1A
FIG. 1B

POLYMERIC SEMICONDUCTORS, DEVICES, AND RELATED METHODS

CROSS-REFERENCE TO RELATED APPLICATIONS

This patent application is a U.S. National Phase under 35 U.S.C §371 of International Application No. PCT/SG2010/000172, filed Apr. 30, 2010, entitled POLYMERIC SEMICONDUCTORS, DEVICES, AND RELATED METHODS, which claims the benefit of and priority from (1) U.S. Provisional Application No. 61/272,182, filed Aug. 28, 2009, the entire contents of which are incorporated herein by reference, and (2) PCT Patent Application No. PCT/SG2009/000393, filed Oct. 22, 2009, the entire contents of which are incorporated herein by reference.

FIELD OF THE INVENTION

The present invention relates generally to semiconductor materials, and particularly to polymeric semiconductors, devices incorporating such polymeric semiconductors, and related methods.

BACKGROUND OF THE INVENTION

Regioregular poly(3-hexylthiophene) (P3HT) or poly(quaterthiophene) (PQT) have been used as semiconductors in organic thin film transistors (OTFT) or organic photovoltaic (OPV) cells. Regioregular P3HT or PQT exhibit a charge mobility of 0.1 to 0.2 cm²/Vs when applied by spin-coating, but significantly lower when applied by a solution-based printing process. Further, P3HT has a wide bandgap of about 1.9 eV. A wider bandgap limits the absorbance of light with higher wavelengths, and consequently the power conversion efficiency (PCE) for sunlight. For example, calculation shows that with a bandgap of 1.9 eV, only about 22% of light with a 650 nm wavelength can be absorbed. It has been reported that the PCE for a P3HT based device is only up to 5% (see Ma, W. L. et al., "Thermally stable, efficient polymer solar cells with nanoscale control of the interpenetrating network morphology," *Adv. Funct. Mater.*, 2005, vol. 15, p. 1617. Narrowing polymeric bandgap can increase the amount of absorbed sunlight, but does not necessarily improve power conversion efficiency, as it can also decrease the equivalent open circuit voltage of the OPV cell. This can lead to a decrease in power conversion efficiency, which offsets the gain from narrowed bandgap. A reported PCE for a device based on known low bandgap polymer OPV materials is only up to 7.73% (see Hsiang-Yu Chen et. al., "Polymer solar cells with enhanced open-circuit voltage and efficiency," *Nature Photonics*, 2009, vol. 3, pp. 649-653.

SUMMARY OF THE INVENTION

It is thus desirable to provide alternative polymers that are suitable for use as semiconductor or photovoltaic materials in electronic devices such as field effect transistors, diodes, or photovoltaic cells.

It is also desirable to provide a polymer that has improved charge mobility.

It is further desirable to provide an alternative polymer that has a low bandgap (<1.9 eV) and can provide improved power conversion efficiency (PCE) in organic photovoltaic (OPV) devices.

Thus, in accordance with an aspect of the present invention, there is provided a polymer comprising a polymeric chain represented by

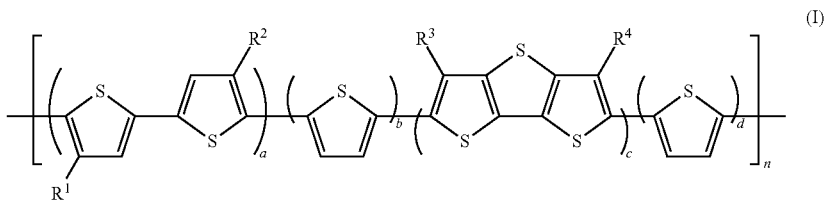

(I)

wherein a, b, c, d, and n are integers, a from 0 to 3, b from 1 to 5, c from 1 to 3, d from 1 to 5, and n from 2 to 5000; and $R^1$ is a first side chain; $R^2$ is a second side chain; $R^3$ is H or a third side chain; $R^4$ is H or a fourth side chain; and wherein when a is 0, $R^3$ and $R^4$ are side chains. At least one of the side chains may have from 6 to 30 backbone atoms; or from 8 to 20 backbone atoms, such as 12 backbone atoms. The polymer may have a number average molecular weight ($M_n$) of from 2,000 to 1,000,000 g/mol, such as from 5,000 to 500,000 g/mol. At least one of the side chains may comprise alkyl, siloxy, alkenyl, alkynyl, amine, ether, carbonyl, ester, amide, sulfonyl, or sulfinyl. The alkyl may have from 1 to 30 carbon atoms, such as from 6 to 20 carbon atoms, or from 12 to 20 carbon atoms. The number n may be from 5 to 1,000. The number a may be 1 to 3, or 0. $R^3$ and $R^4$ may be both H.

In accordance with another aspect of the present invention, there is provided a polymer polymer comprising a polymeric chain represented by

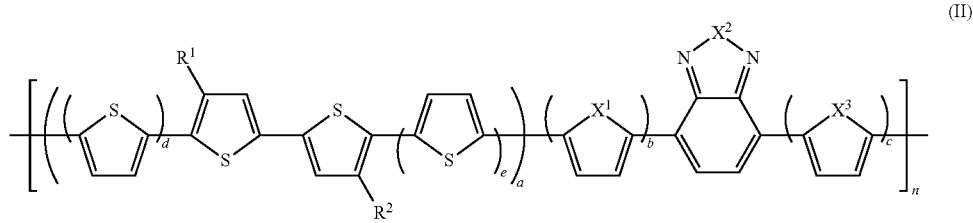

(II)

wherein a, b, c, d, e, and n are integers, a from 1 to 3, each of b and c being independently 0 or 1, each of d and e being independently 1 or 2, and n from 2 to 5000; $R^1$ is a first side chain except —COOalkyl; $R^2$ is a second side chain except —COOalkyl; and each of $X^1$, $X^2$ and $X^3$ is independently O, S, or Se. At least one of the side chains may have from 6 to 30 backbone atoms, such as from 8 to 20 backbone atoms. The polymer may have a number average molecular weight ($M_n$) of from 2,000 to 1,000,000 g/mol, such as from 5,000 to 500,000 g/mol. The number n may be from 5 to 1,000, such as from 10 to 1,000. At least one of the side chains may comprise alkyl, siloxy, alkenyl, alkynyl, amine, ether, carbonyl, amide, sulfonyl, or sulfinyl. The alkyl may have from 1 to 30 carbon atoms. Each of $X^1$, $X^2$, and $X^3$ may be S.

In accordance with a further aspect of the present invention, there is provided a semiconductor comprising a polymer described herein.

In accordance with another aspect of the present invention, there is provided an electronic device comprising the semiconductor described herein. The device may comprise a thin film transistor.

In accordance with a further aspect of the present invention, there is provided a device comprising a polymer described herein. The device may comprise a thin film transistor, photovoltaic cell, photodiode, light-emission diode, sensor, or memory. The photovoltaic cell may comprise a layer formed of a mixture of the polymer and phenyl-$C_m$-butyric acid methyl ester (PCBM), where m=61 or 71. The weight ratio of the polymer to the PCBM in the layer may be from about 2:1 to about 1:5.

In accordance with another aspect of the present invention, there is provided a process for forming a device described herein. The process comprises dissolving the polymer in a solution; applying the solution to a substrate; and drying the solution to form a solid layer comprising the polymer.

Conveniently, an exemplary embodiment of the polymers disclosed herein can exhibit improved charge mobility, such as up to about 0.5 cm²/Vs. It is expected that when this particular polymer is applied to form a semiconductor in a solution-based printing process, the charge mobility could remain higher than 0.1 cm²/Vs. It has been found that a semiconductor formed from such a polymer may have an increased current on/off ratio, as compared to regioregular poly(3-hexylthiophene) (P3HT) or poly(quaterthiophene) (PQT).

Another exemplary embodiment of the polymers disclosed herein can have a bandgap lower than 1.9 eV, such as below 1.7 or 1.6 eV, and can have improved light absorption efficiency as compared to P3HT. This particular polymer can be conveniently processed to achieve sufficient charge separation and provide sufficient charge transport across the polymer material, so that the resulting material is suitable for use in OPV devices. Such a polymer can exhibit improved power conversion efficiency (PCE) as compared to P3HT and some low bandgap polymeric materials.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention, FIGS. 1A, 1B, 2A, and 2B show chemical formulas for polymers exemplary of embodiments of the present invention;

DETAILED DESCRIPTION

Figure 2A:
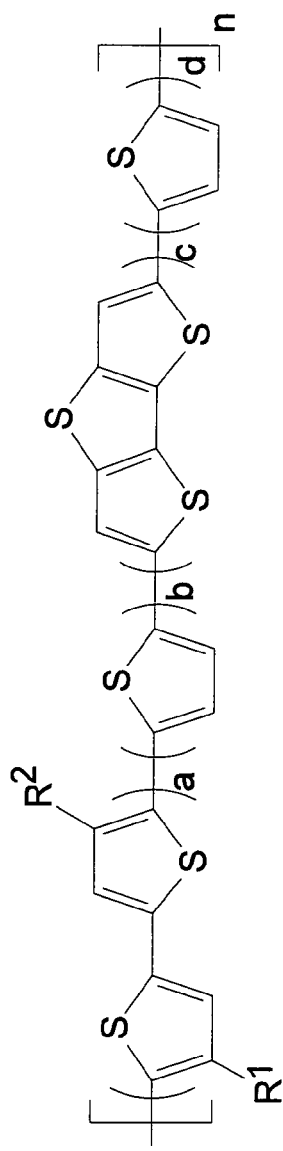

A first exemplary embodiment of present invention relates to a polymer comprising a polymeric chain represented by the formula shown in FIG. 1A, referred to herein as formula (I).

In formula (I), a, b, c, d, and n are integers, where a is from 0 to 3, c is from 1 to 3, b and d are each independently from 1 to 5, and n is from 2 to 5000, such as from 5 to 1000 or 10 to 1000.

In formula (I), each of $R^1$ and $R^2$ is a side chain, and each of $R^3$ and $R^4$ is H or a side chain. Subject to the restriction that $R^3$ and $R^4$ are side chains when a=0, $R^1$, $R^2$, $R^3$, $R^4$ may be otherwise independently selected. One or more of the side chains may each independently have from 10 to 30 backbone atoms, such as 12 to 20 backbone atoms or 12 backbone atoms. The side chains may also have from 6 to 20, 12 to 20, or 12 to 25 backbone atoms.

The polymer may have a number average molecular weight ($M_n$) of from 2,000 to 1,000,000 g/mol, such as from 5,000 to 500,000 g/mol.

A side chain may comprise alkyl, siloxy, alkenyl, alkynyl, amine, ether, carbonyl, ester, amide, sulphide, sulfonyl, sulfinyl, organosilane, or thiolate. Each of these listed groups may include a derivative of the group or a substituted group. A side chain may be linear or branched. In some embodiments, the side chains may be linear alkyl chains. As further described elsewhere herein, the side chains are selected and positioned to provide improved solubility and packing of the polymer molecules during use.

The alkyl may have from 1 to 30 carbon atoms, such as from 6 to 30 or from 12 to 25 carbon atoms. Suitable alkyls also include alkoxyalkyl, siloxyl-substituted alkyl, perhaloalkyl, halogen-substituted alkyl, or nitrile-substituted alkyl.

Ether may include a polyether, such as oligoethylene oxide, or thioether. Ester may be a carbonate ester. A side chain may also include substituted amine, thiocarbonyl, carboxylic ester, thioester, thioamide, or the like.

Depending on the context, an alkyl may be branched or linear, and may have 1 to 30 carbon atoms. Examples of alkyl groups include methyl, ethyl, n-propyl, isopropyl, n-butyl, isobutyl, t-butyl, sec-butyl, pentyl, hexyl, heptyl, octyl, nonyl, decyl, undecyl, dodecyl, tridecyl, tetradecyl, pentaceyl, hexadecyl, heptadecyl, octadecyl, nonadecyl, eicosyl, etc. An alkyl group may be unsubstituted, or optionally substituted with one or more substituents.

Any substituent in the polymer, unless otherwise specified, may be halogen or nitrile.

For the alkyl group, the substituent may also be a lower alkyl. A "lower" group has 1 to 6 carbon atoms, such as 1 to 4 carbon atoms. Examples of lower alkyl groups include, but are not limited to, methyl, ethyl, n-propyl, i-propyl, n-butyl, i-butyl, sec-butyl, t-butyl, pentyl, and hexyl. A lower alkyl group may be unsubstituted or optionally substituted with one or more substituents. The substituents may include halogen, nitrile, $CF_3$, $CCl_3$, $CBr_3$, $Cl_3$, $C_2F_5$, $C_3F_7$, $C_4H_9$, or the like.

The substituted alkyl groups may include haloalkyl groups.

Examples of the groups that may be included in the side chains include $CF_3$, $CCl_3$, $CBr_3$, $Cl_3$, $C_2F_5$, $C_3F_7$, $C_4H_9$, $C_5F_{11}$, $C_6H_{13}$, $C_7H_{15}$, $C_8H_{17}$, $C_9F_{19}$, $C_{10}F_{21}$, $C_{11}F_{23}$, $C_{12}F_{25}$, $C_{14}F_{29}$, $C_{16}F_{33}$, $CF_2CH_3$, $CF_2C_2H_5$, $CF_2C_3H_7$, $CF_2C_4H_9$, $CF_2C_5H_{11}$, $CF_2C_7H_{15}$, $CF_2C_{11}C_{23}$, $CCl_2C_{11}H_{23}$, $—CBr_2C_{11}H_{23}$, $CCl_2C_{11}H_{23}$, $CF_2C_{13}H_{27}$, $CF_2C_{15}H_{31}$, or the like. Other substituted alkyl groups include 2-methylhexyl, 2-ethylhexyl, 3,7,7-trimethyloctyl, 2-ethyl-2-propylhexyl, 2-butyloctyl, 2,2-dimethyldecyl, 7-methyl-4-(1-methylethyl)octyl, 2-methyldodecyl, 11-methyldodecyl, 2-ethyldodecyl, 3-ethyldodecyl, 4-ethyldodecyl, 2-butyldecyl, 2-hexyloctyl, 2-pentylnonyl, 4-pentylnonyl, 3,7,11-trimethyldodecyl, 2-butyldodecyl, 1-methylpentadecyl, 2-hexyldecyl, 2-(1,3,3-trimethylbutyl)-5,7,7-trimethyloctyl, 2-hexyldodecyl, 2-octyldecyl, 1,1-dimethylhexadecyl, 2-octyldodecyl, 4-octyldodecyl, 2-decyltetradecyl, 4-decyltetradecyl, or the like.

An alkenyl may be branched or linear, may have 2 to 20 carbon atoms, and has one or more double carbon bonds. Examples of alkenyl groups include ethenyl, propenyl, butenyl, penentyl, hexenyl, heptenyl, nonenyl, decenyl, or the like. An alkenyl group may be unsubstituted or optionally substituted with one or more substituents.

An alkynyl may be branched or linear, and may have 2 to 20 carbon atoms, and has one or more triple carbon bonds. Examples of alkynyl groups include ethynyl, propynyl, butynyl, penyntyl, hexynyl, heptynyl, nonynyl, decynyl, or the like. An alkenyl group may be unsubstituted, or optionally substituted with one or more substituents.

Amine or amino is a group that includes —NH— or —NR—, where R may be an alkyl group. A carbonyl is a group that includes —(C=O)—. Ester is a group that includes —(C=O)O— or —O(C=O)—. Carbonate ester is a group that includes —O(C=O)O—. Ether is a group that includes —O—. Sulphide is a group that includes —S—. Organosilane is a group that includes —$SiR^OR^{OO}$—, wherein $R^O$ and $R^{OO}$ may each be H, a lower alkyl, or the like. Thioate is a group that includes —S(C=O)— or —(C=S)—. Halo or halogen may be F, Cl, Br, or I. Nitrile is a group that includes —C≡N.

In different embodiments, a side chain may also be an heteroalkyl, heteroalkenyl, or heteroalkynyl. A heteroatom in the side chains may be selected from N, O, S, P, Si, Cl, Br, I, or the like. The side chains may also include cyclic rings, such as 5-, 6- or more membered rings. For example, the side chains may include cycloalkyl, cycloakenyl cycloalkynyl, or the like, or their heterocyclo counter parts. However, when the side chains include the above polymer groups, the side chains should be selected so that they include different polymeric chains and are not too bulky. When the side chains are similar bulky chains, they will negatively affect the film morphology when the resulting composition is used to form films.

In one embodiment, a is 1 to 3, and $R^3$ and $R^4$ are both side chains.

In another embodiment, a is 1 to 3, and $R^3$ and $R^4$ are both H. In this case, the polymer chain may be represented by the formula shown in FIG. 2A, referred to as formula (IA) herein.

Figure 2B:
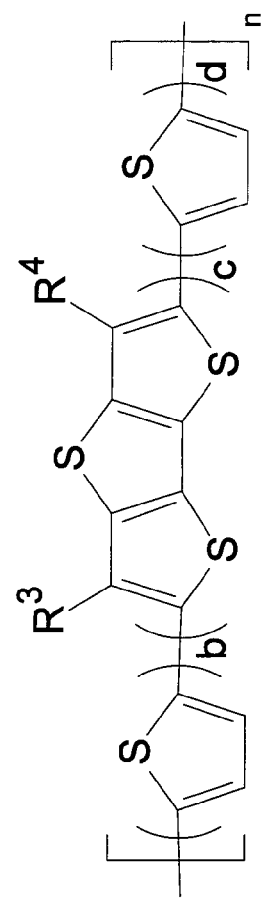

In a further embodiment, a is 0, and $R^3$ and $R^4$ are both side chains. In this case, the polymer chain may be represented by formula of FIG. 2B, referred to as formula (IB) herein.

A polymer comprising the polymeric chain of formula (I), (IA), or (IB), is referred to as polymer (I), polymer (IA), or polymer (IB) respectively herein.

As can be appreciated, the backbone of each of polymer (I) is formed of repeating thienylene units (including thienylene, bithienylene, and dithienothiophene units), and at least some of the repeating units have side chains positioned in a regioregular manner on the polymer backbone. The S in the backbone may serve as electron donors. Side chains in regioregular positions can facilitate self-alignment of the polymer chains under suitable processing conditions, such as in a solution. In turn, proper molecular alignment permits enhanced molecular structural order to be achieved, such as in a thin film, and the enhanced structural order facilitates efficient charge carrier transport in the film.

Thus, conveniently, the polymer chains can self-align in a solution and can self-organize into a densely packed structure in both solutions and thin films, thus resulting in a semiconductor with charge mobility higher than 0.1 cm$^2$/Vs, such as from about 0.1 to about 0.5 cm$^2$/Vs.

The charge mobility in a material may be measured by using a TFT device configuration wherein the material to be measured forms the semiconductor channel between the drain and the source. The TFT device may be characterized using a Keithley SCS-4200™ probe station under an ambient environment in dark. The field effect mobility (μ) can be extracted using the following equation in the saturation regime from a gate sweep:

$$I_{SD} = \mu C_i (V_G - V_T)^2 (W/2L)$$

where $I_{SD}$ is the drain current, $C_i$ is the capacitance per unit area of the gate dielectric layer (SiO$_2$, 200 nm, Ci=17.25 nF/cm$^2$), and $V_G$ and $V_T$ are respectively gate voltage and threshold voltage. $V_T$ was derived from the relationship between the square root of $I_{SD}$ at the saturated regime and $V_G$ by extrapolating the measured data to $I_{SD}$=0. W and L are respectively channel width and length. $I_{on}/I_{off}$ is the ratio of the saturation source-drain current when the gate voltage $V_G$ is equal to or greater than the drain voltage $V_D$ to the source-drain current when the gate voltage $V_G$ is zero.

Without being limited to any particular theory, it is expected that the improved charge mobility results from the densely packed and ordered structures of the polymer, such as in a thin film layer after deposition, through strong π-π stacking among the polymer backbones. For instance, in the exemplary polymer of formula (I) the backbone formed of thienylene (including bithienylene and dithienothienylene) repeat units may form dense and ordered structures. The resulting charge mobility exhibited by test samples of the semiconductor is sufficiently high for use in organic electronic device applications.

The backbone forms an ordered structure through strong π-π stacking. The presence of the bithienylene and dithienothienylene repeat units with the side chains allows solution processability of the polymer; while the thienylene repeat units without side chains provide sufficient flexibility for the polymer chain to rotate during packing, thus facilitating ordering of the packed polymer structure when the polymer is applied during use.

As can be seen in FIG. 1A, the backbone groups with the side chains are regioregular or substantially regioregular. However, to prevent or reduce potential steric hindrance of, and interference with, efficient and orderly packing of the polymer during application, the side chains are selected to avoid or limit head-to-head linkage between adjacent side chains.

The lengths of the side chains (as measured by the number of backbone atoms in each side chain) are selected so that they are not too long or too short. On one hand, as the solubility of the polymer depends on the length of the side chains, when the lengths of the side chains are too short, the solubility of the polymer will be poor. On the other hand, as the likelihood of aggregation of the polymer increases with increasing lengths of the side chains, when the lengths of the side chains are too long, the polymer will tend to aggregate and even precipitate in a solution. Thus, in an embodiment, the lengths of the side chains are selected to be the shortest possible lengths that provide the desired solubility in a selected solvent, where the solvent may be an organic solvent or water. In this case, the side chains in the polymer may have the same length or substantially the same length. Of course, in different embodiments or applications, the lengths of the side chains may vary between different polymers or within the same polymer. A person skilled in the art can readily test whether polymers are suitably soluble in a given solvent, or whether or how the polymers will aggregate or precipitate in the solvent. Thus, the skilled person can readily adjust the side chain lengths as needed in any particular application.

Polymer (I) may be prepared by a polymerization technique, such as Stille coupling, Suzuki coupling, or $FeCl_3$ mediated oxidative coupling, that does not require regioregular coupling reaction. In comparison, the preparation of regioregular polythiophenes, such as poly(3-alkylthiophene-2,5-diyl), requires regioregular coupling reaction, which can cause regioregularity complications.

Figure 3:
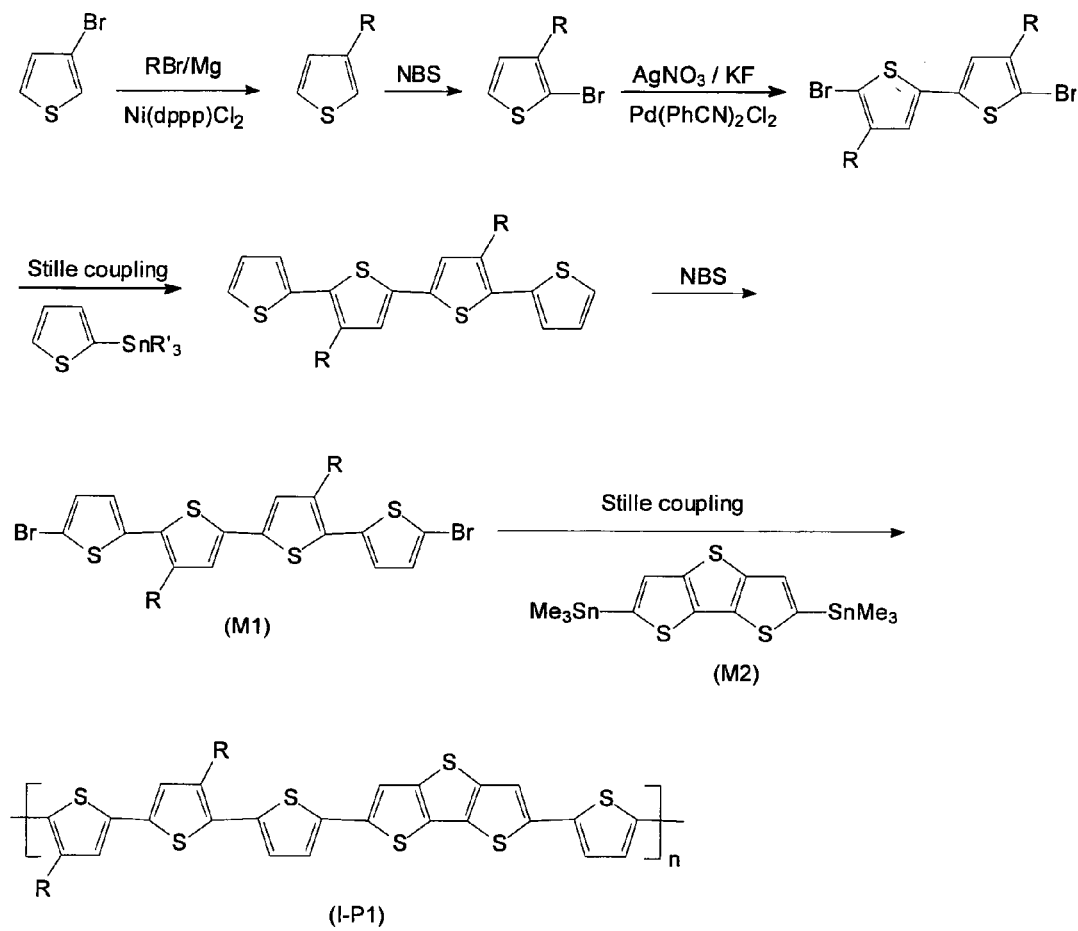
FIG. 3 is a schematic diagram showing a synthesis route for forming a polymer shown in FIGS. 1A and 2A, exemplary of embodiments of the present invention.

For example, in an exemplary embodiment of the present invention, a specific example of polymer (I), polymer (I-P1) shown in FIG. 3, may be prepared according to the synthesis process illustrated in FIG. 3. Formula (I) reduces to formula (I-P1), when a=b=c=d=1, $R^1$=$R^2$=R, and $R^3$=$R^4$=H. R may be any of the side chains described herein for $R^1$, $R^2$, and each R may be independently selected.

As shown in FIG. 3, polymer (I-P1) may be formed by Stille coupling reaction of oligothiophene monomer and dithienothiophene distannanyl monomer.

Precursor monomer (M1) for oligothiophene can be formed from the reaction of 4,4'-di-substituted 5,5'-dibromo-2,2'-bithiophene with 2-stannanyl-thiophene through Stille coupling reaction followed by N-bromosuccinimide (NBS) bromination, as illustrated in FIG. 3.

2,6-Bis-trimethylstannanyl-dithieno[3,2-b;2',3'-d]thiophene (M2) may be synthesized according to the procedure described in J. Frey et al., *Chem. Commun.* 2002, vol. 20, pp. 2424-2425, the entire contents of which are incorporated herein by reference.

The positions of side chains on precursor monomer (M1) ensure that in the resultant polymer (I-P1) the side chains (R) are regioregularly positioned on the backbone.

Positioning of the side chains R may be effected in the preparation process of monomer (M1) such as by following the procedure illustrated on the top of FIG. 3. See also M. Takahashi et al., "Palladium-Catalyzed C—H Homocoupling of Bromothiophene Derivatives and Synthetic Application to Well-Defined Oligothiophenes," *J. Am. Chem. Soc.*, 2006, vol. 128, pp. 10930-10933, the entire contents of which are incorporated herein by reference.

As will be understood by the skilled person, the values of a-c and d can be controlled during the synthesis process according to known techniques. For example, different combinations of values of a, b, c, and d can be obtained by following different synthetic procedures. The value of n can be controlled by known techniques, including, for example, adjusting reaction time or reaction temperature, selection of solvent and catalyst, and varying the molar ratio of the different monomers in the reaction mixture.

Polymer IB may also be prepared based on Stille coupling. For example, polymer IB may be prepared as follows. The di-stannanyl derivative of thiophene (or bithiophene, or both), 2,6-dibromo-3,5-dialkyl-dithieno[3,2-b;2',3'-d]thiophene, tri (o-tolyl)phosphine, tris(dibenzylideneacetone)dipalladium and dry chlorobenzene are added to a Schlenk flask under nitrogen. The total amount of the di-stannanyl compounds added are equimolar to the amount of di-bromo compound used in the reaction. The flask is securely sealed and stirred for 72 h at 120° C. After cooling to room temperature, the reaction mixture is precipitated into a mixture of methanol and concentrated hydrochloric acid, and stirred for 16 h. The precipitate is collected, then Soxhlet extracted sequentially with ethanol, hexane and chloroform. The chloroform fraction is collected and dried under vacuum to produce polymer IB.

Further details of the synthesis procedure are illustrated in the Examples.

A polymer represented by formula (I) may be conveniently used to form semiconductors or charge transport materials. These materials may be used in an electronic device, such as a field-effect transistor (FET), thin film transistor (TFT), organic TFT (OTFT), organic light emitting diode (OLEDs), or organic photovoltaic diode.

Figure 4:
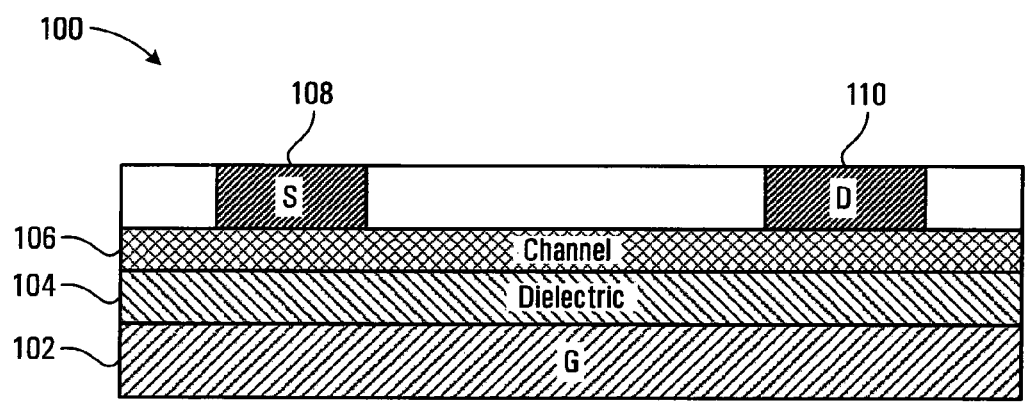
FIG. 4 is a cross-sectional elevation view of an organic field effect transistor (OFET), exemplary of an embodiment of the present invention.

For example, the polymer may be used as a semiconductor material or dielectric material in a thin film transistor (TFT), as illustrated in FIG. 4.

FIG. 4 illustrates a TFT 100 that includes a gate layer 102. A dielectric layer 104 is formed on gate layer 102. A semiconductor layer 106 is formed on dielectric layer 104. A source electrode 108 and a drain electrode 110 are on top of, and in contact with, semiconductor layer 104. Semiconductor layer 104 is formed of the polymer of formula (I).

In other embodiments, the structure of the TFT may vary from that of TFT 100 as depicted in FIG. 4, as can be understood by those skilled in the art. Other than using the semiconductor polymer as described herein, TFT 100 and its possible variations may be structured in accordance with known TFT techniques.

For example, in a possible variation, a substrate (not shown) may be provided. The semiconductor layer may be formed on the substrate, and the dielectric layer may be formed on the semiconductor layer. The gate layer may be formed on top of the dielectric layer. Source and drain electrodes may be formed on the substrate or embedded in the semiconductor layer.

Additional layers and components, such as insulation layers may also be provided in different embodiments.

Conveniently, semiconductor 106 may be formed using a solution based process, such as spin coating, stamp printing, screen printing, or jet printing. Other components of TFT 100, such as the source, drain, and gate electrodes, and the dielectric layer may also be formed in a solution-based process, such as by spin coating, solution casting, stamp printing, screen printing, or jet printing. A solution based process may also include dip coating.

For this purpose, the semiconductor polymer may be configured so that the solubility of the polymer in an organic solvent is above about 0.1 wt % (weight percent), where the solvent may be a solvent commonly used in fabrication processes of electronic devices, such as chloroform, tetrahydrofuran (THF), toluene, xylene, mesitylene, chlorobenzene, dichlorobenzene, or the like. As a result, the polymer may be conveniently fabricated into electronic devices through the solution-based processes.

Electrodes 108 and 110 may be formed of gold, nickel, aluminum, platinum, indium titanium oxide, conductive polymer, or a conductive composition. The conductive polymer may be polystyrene sulfonate-doped poly(3,4-ethylene dioxythiophene). The conductive composition may include ink/paste compound formed from a colloidal dispersion of silver in a polymer binder. Different electrodes may be formed of the same or different materials, which may be independently selected.

Dielectric layer 104 may be formed of silicon nitride, silicon oxide, an organic polymer, or an inorganic oxide particle-polymer composite. The organic polymer may be poly(methyl methacrylate) or poly(vinyl phenol).

In one embodiment, dielectric layer 104 may be formed of silicon oxide, and gate layer 102 may be formed of n-doped or p-doped silicon.

The various layers and electrodes of TFT 100 may have any suitable thickness or size. In a particular embodiment, gate layer 102 may be formed of $n^+$-Si or $p^+$-Si. Dielectric layer 104 may be made of $SiO_2$ and may have a thickness of about 200 nm. Semiconductor layer 106 may be a thin film of the polymer with a thickness of about 35 to about 40 nm. Source and drain electrodes 108, 110 may be formed of Au, and may be of a thickness of about 100 nm.

Semiconductor layer 106 may be grown on top of the $SiO_2$ dielectric layer 104 by spin coating. An Au layer may be deposited on semiconductor layer 106 using a shadow mask to form source and drain electrodes 108, 110.

It is expected that a device containing the semiconductor polymer can exhibit enhanced resistance to adverse effects of oxygen. Without being limited to any particular theory, it is expected that semiconducting polymers with high HOMO energy levels (for example, HOMO>−5.0 eV) can be more easily attacked by oxygen. Oxidized species in the polymer chain can trap charge carriers and thus lower the charge mobility of the polymer. Further, oxidation may lead to material degradation. When the HOMO energy levels are lowered, such as to or below about −5.15 eV, the polymer is more resistant to oxygen attack. The HOMO energy level in the polymers described herein may be controlled to be less than −5.1 eV. According to some, embodiments, the HOMO energy level is controlled by controlling the polymer backbone structure, and the linkage between side chains. For example, it is expected that when dithienothiophene units are incorporated into the backbone chain alkyl groups are incorporated onto the dithienothiophene units, the resulting polymer can have the desired low HOMO levels. As a result, the useful lifetime of the device can be increased.

With the specified structures of the polymer, it is also possible to control the extended π-conjugation and substitution pattern in the polymer, such as to achieve a balance between transistor functionality and oxidative doping stability.

Tests have also demonstrated that a device formed of sample semiconductor polymer exhibited relatively high current on/off ratio, such as about $10^4$. It is expected that the on/off ratio of an embodiment of the present invention can be as high as above $10^8$.

A TFT, such as TFT 100, or OTFT, may be formed according to the following procedure.

A substrate formed from a layer of $n^+$-Si or $p^+$-Si and a layer of $SiO_2$ may be obtained. Such substrates of different dimensions may be available from commercial sources in the form of wafers. The substrate may be cleaned, such as by ultrasonication in acetone, methanol, and de-ionized water. The cleaned substrate may be dried under a flow of nitrogen at a temperature of about 100° C. for about 5 minutes. The dried substrate may then be subject to UV-ozone treatment for about 20 minutes.

The substrates may also be surface treated to improve alignment of the semiconductor polymer on the surface. For example, the substrate may be subject to SAM (self-assembled monolayer) treatment as described in A. Salleo et al., "Polymer thin-film transistors with chemically modified dielectric interfaces," *Appl. Phys. Lett.*, 2002, vol. 81, no. 23, pp. 4383-4385, the entire contents of which are incorporated herein by reference. For example, octyltrichlorosilane (OTS) SAM treatment may be carried out as follows. A few drops of OTS are placed on the surface of the substrate and the substrate is then placed in a desiccator. The dessicator may be subjected to vacuum and heating, such as at 110° C. for three hours. After heating, the substrate may be removed and rinsed with isopropanol and dried under flow of nitrogen gas.

A thin film of the polymer may be next grown on the substrate by a solution-based coating processing, such as spin coating. The polymer solution may be a solution of the polymer in an organic solvent such as chlorobenzene.

The solution film on the substrate surface may be annealed at a suitable temperature, such as at 80, 120, 160, or 200° C.

Next, gold contacts may be deposited on the dried thin film using a shadow mask. The resulting OTFT devices may have different channel lengths, depending on the placement of the source and drain electrodes. For example, the channel length may be 50, 100, or 200 μm. The channel width may be 1 mm or 3 mm.

Another exemplary embodiment relates to a semiconductor polymer that has a polymeric chain represented by the formula shown in FIG. 1B, referred to herein as formula (II). The polymer of formula (II) is referred to as polymer (II) herein.

In formula (II), a, b, c, d, e, and n are integers, where a is from 1 to 3, b and c are independently 0 or 1, d and e are independently 1 or 2, and n is from 2 to 5000.

In formula (II), $R^1$ and $R^2$ are side chains, and may be selected as discussed above for $R^1$ and $R^2$ in formula (I), unless otherwise expressly specified below.

$X^1$, $X^2$, and $X^3$ are independently O, S, or Se. In one embodiment, $X^1$, $X^2$, and $X^3$ may each be S. O, S, or Se are selected for their good electron donating properties.

In one embodiment, a side chain $R^1$ or $R^2$ may have from 12 to 25 backbone atoms.

Polymer (II) may have a number average molecular weight ($M_n$) of from 2,000 to 500,000 g/mol, or a weight average molecular weight ($M_w$) of from 4,000 to 2,000,000 g/mol. For example, $M_n$ of polymer (II) may be from 5,000 to 200,000 g/mol; or $M_w$ of polymer (II) may be from 10,000 to 500,000 g/mol.

In some embodiments, n may be from 5 to 1000, or 10 to 1,000 in polymer (II).

Figure 5:
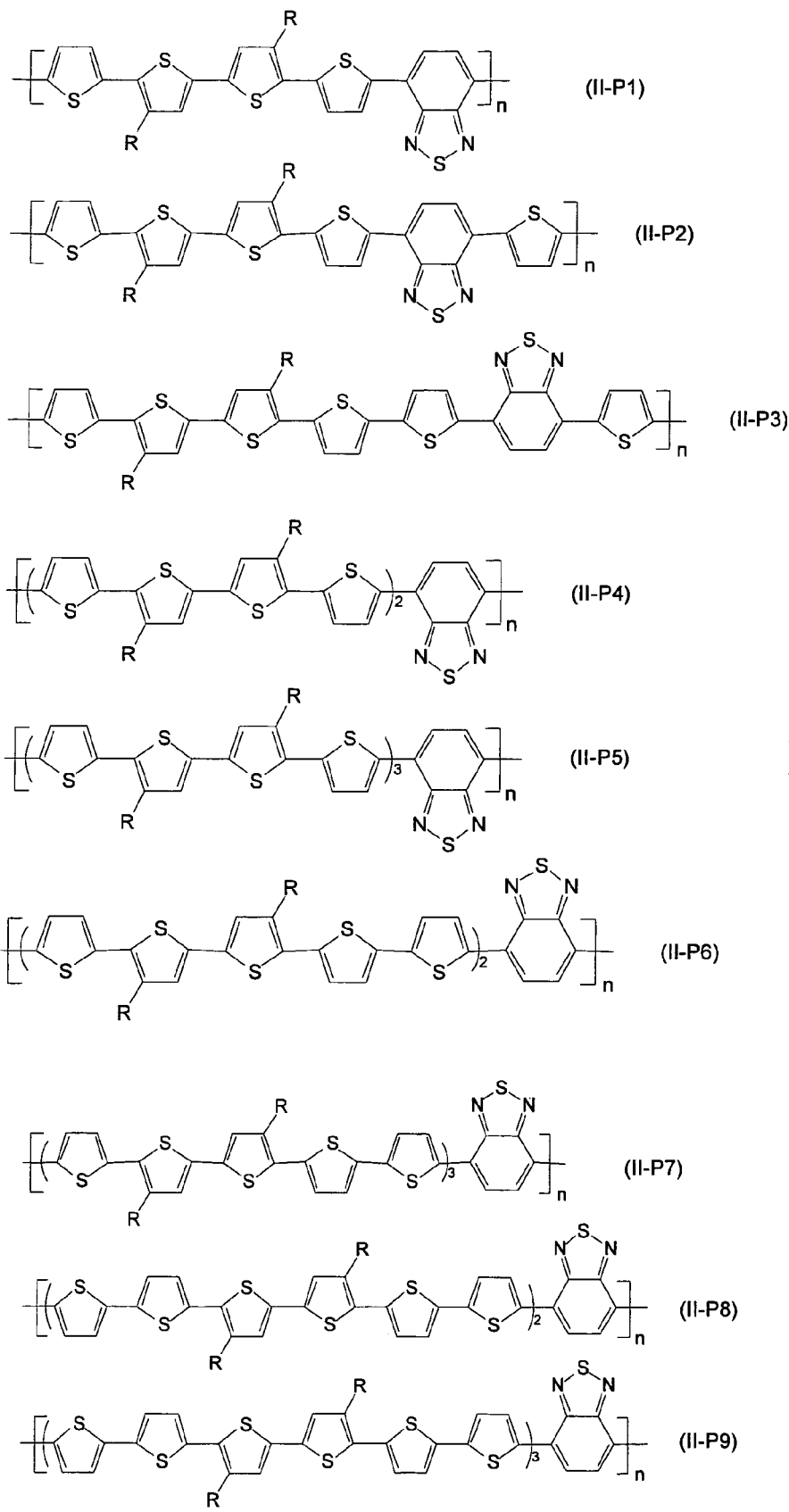
FIG. 5 shows chemical formulas for polymers exemplary of embodiments of the present invention.

Some specific examples of polymer (II), polymers (II-P1) to (II-P9), are shown in FIG. 5, where R can be any of the side chains for $R^1$ or $R^2$ described herein, and each R may be independently selected.

In one embodiment, polymer (II) is polymer (II-P1). In another embodiment, polymer (II) is polymer (II-P2). In another embodiment, polymer (II) is polymer (II-P3). In another embodiment, polymer (II) is polymer (II-P4). In another embodiment, polymer (II) is polymer (II-P5). In another embodiment, polymer (II) is polymer (II-P6). In another embodiment, polymer (II) is polymer (II-P7). In another embodiment, polymer (II) is polymer (II-P8). In another embodiment, polymer (II) is polymer (II-P9).

In exemplary embodiments of formula (II), side chains $R^1$ and $R^2$ are not —COOalkyl. In particular, in these embodiments, formula (II) excludes the following:

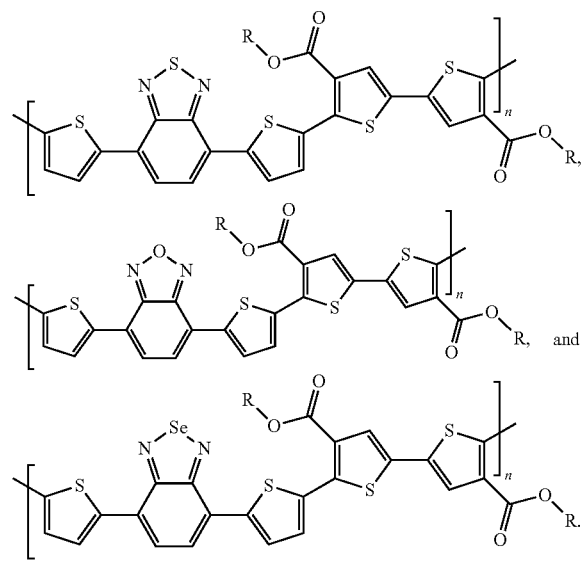

In further exemplary embodiments of formula (II), side chains $R^1$ and $R^2$ are selected so that the substituted di-thiophene moiety as a whole is not an electron acceptor group. In these embodiments, the substituted di-thiophene moiety as a whole may be an electron donating group. For example, when $R^1$ and $R^2$ are alkyl chains, the substituted di-thiophene moiety as a whole is an electron &mating group.

As used herein when describing either electron accepting (withdrawing) or electron donating character of a particular aromatic or heteroaromatic group, such terms are used relative to the reference group of an unsubstituted phenyl group, either monovalent or divalent depending on whether the relevant group is a terminal group or falls within the backbone chain. Benzene is weakly electron donating, and thus electron donating aromatic or heteroaromatic groups described herein have equivalent or greater electron donating character as compared to a phenyl group. In contrast, electron accepting aromatic or heteroaromatic groups described herein have less electron donating character as compared to a phenyl group. Thus, when a given aromatic or heteroaromatic group is conjugated to a phenyl group, if the pi electron cloud of the phenyl group moves toward the given aromatic or heteroaromatic group, the group is considered to be electron withdrawing; otherwise, the group is considered to be electron donating. Conventional methods and techniques can be used to determine whether a pi electron cloud of a phenyl group moves toward a given aromatic or heteroaromatic group, including electrophilic substitution reactions, or theoretical calculations of electron density. The term "conjugated" as used herein in reference to the backbone of a molecule refers to a molecule having two or more pi bonds in the main chain of the molecule, each pi bond being separated from the next consecutive pi bond by a single bond so that π orbitals overlap not only across the pi bond, but also across adjacent single bonds located between adjacent pi bonds.

A further exemplary embodiment relates to a process for preparation of exemplary embodiments of polymer (II). Polymer (II) can be conveniently prepared through Stille coupling, Suzuki coupling, reduction, oxidation reaction, or the like.

Figure 6:
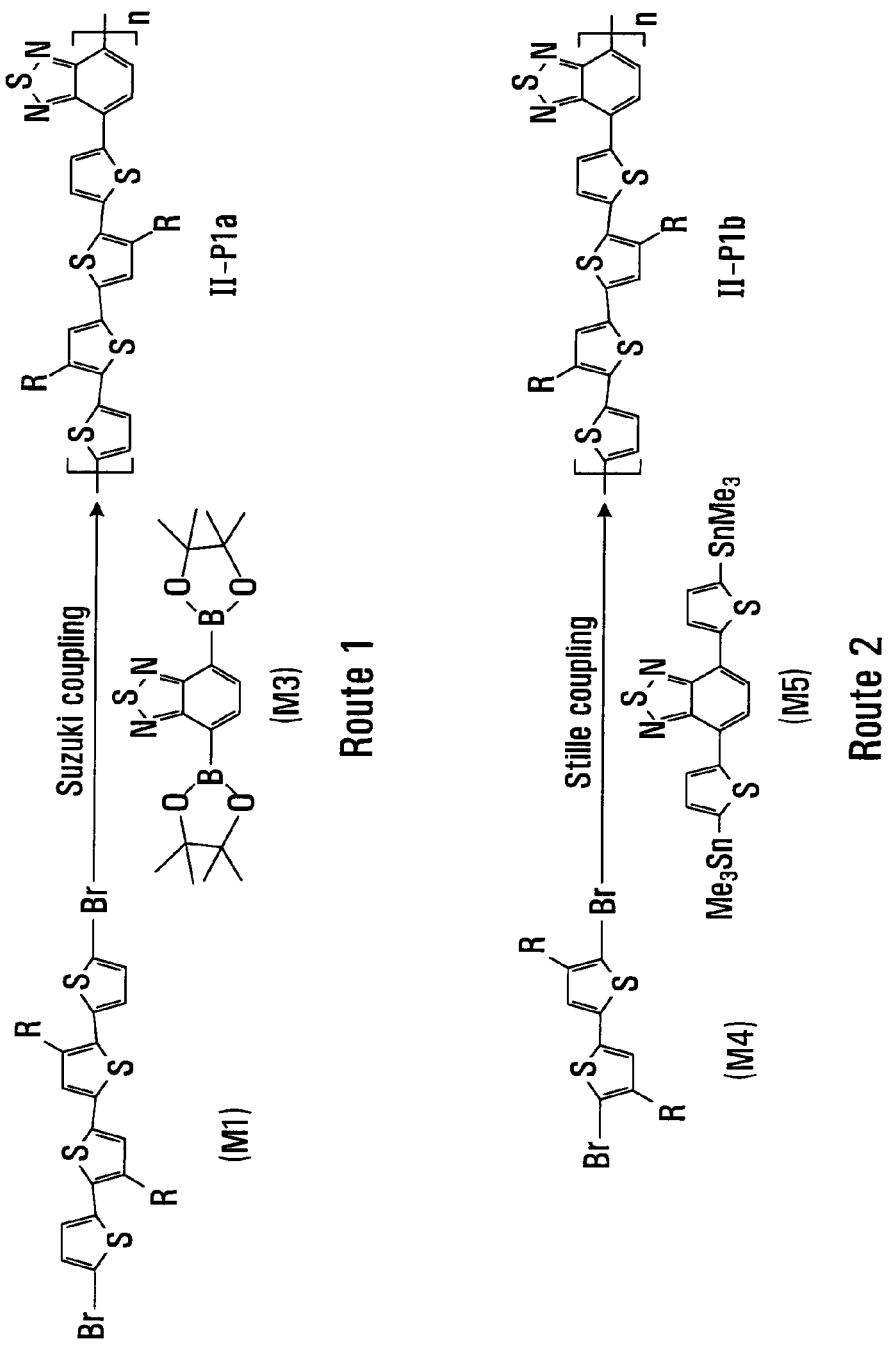
FIGS. 6 and 7 are schematic diagrams showing synthesis routes for forming polymers shown in FIGS. 1B and 5, exemplary of embodiments of the present invention.

For example, polymers (II-P1) can be prepared from suitably constructed oligothiophene monomers, as illustrated in FIG. 6, through Suzuki coupling reaction or Stille coupling reaction.

In Route 1 of FIG. 6, polymer (II-P1a) is formed from monomers (M1) and (M3) through Suzuki coupling reaction. Monomer (M1) may be prepared as discussed earlier, and illustrated in FIG. 3.

In Route 2 of FIG. 6, polymer (II-P1b) is formed from monomers (M4) and (M5) through Stille coupling reaction. Monomer (M4) may be prepared as discussed earlier, and illustrated in FIG. 3.

Figure 7:
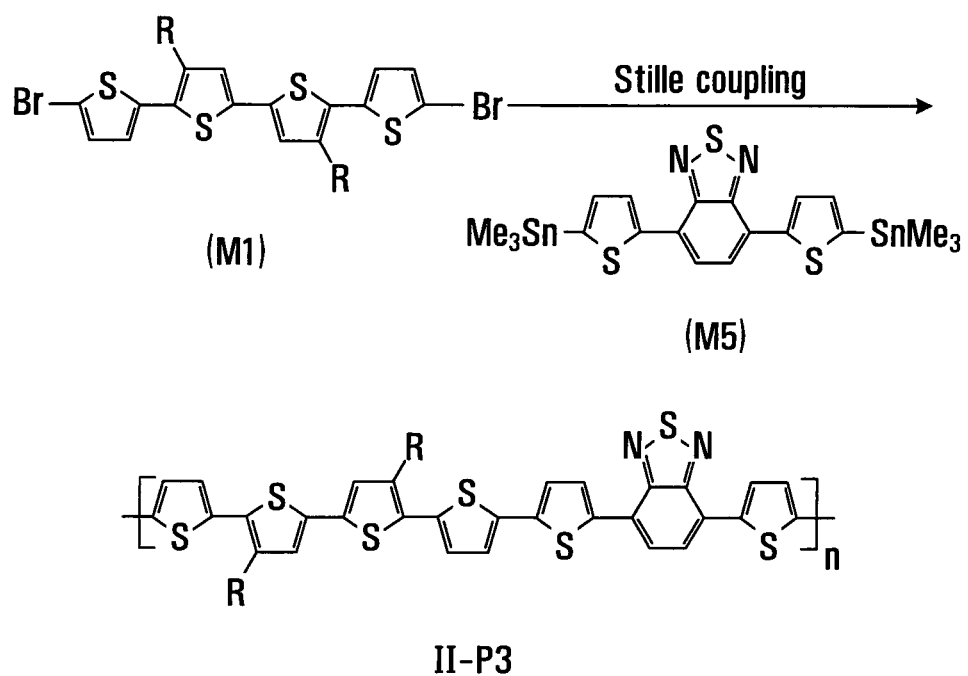

Polymer (II-P3) may be prepared according to the exemplary synthesis process illustrated in FIG. 7 through Stille coupling. Monomers (M1) and (M5) may be prepared or obtained as discussed before.

Further details for these exemplary synthesis routes are discussed in the Examples. The reagents and monomers used in the synthesis routes shown in FIGS. 6 and 7 may be prepared or obtained as described in the examples, or in any other suitable manner know to those skilled in the art.

As discussed above regarding polymer (I), the side chains in the resulting polymer (II-P1) or (II-P3) are also regioregularly positioned along the backbone. The side chain positions may be controlled by selecting suitable monomers such as monomers (M1) or (M4).

Semiconductor polymers with side chains in regioregular positions can facilitate self-alignment of the polymer chains under suitable processing conditions.

As polymer (II) contains electron-rich (donor) oligothiophene blocks and electron-deficient (acceptor) benzothiadiazole blocks, polymer (II) may be used in an electronic device, such as to form a p-type semiconductor or layer. The semiconductor layer may also include an n-type material.

Exemplary embodiments of polymer (II) may have a bandgap below 1.9 eV, such as below about 1.6 or 1.7 eV. Such a polymer can be used in an OPV application to cover broader sunlight spectra than a polymer with wider (higher) bandgap, such as P3HT.

The side chains in polymer (II) may be selected to improve solubility of the polymer in organic solvents, such as chloroform, tetrahydrofuran (THF), toluene, xylene, mesitylene, chlorobenzene, dichlorobenzene, or the like, which are commonly used in semiconductor industry. For example, for improved solubility, the side chains may be branched: To be soluble in organic solvents, the side chains may be lipophilic. To be soluble in aqueous solutions, the side chains may be hydrophilic. The side chains may also be selected to improve miscibility of polymer (II) with n-type semiconductor materials, such as PCBM (phenyl-$C_m$-butyric acid methyl ester, where m=61 or 71). Such miscibility facilitates formation of a bi-continuous network structure in the solution, thus improving charge separation and transporting properties of the composite.

For example, the side chains may be selected so that polymer (II) may have a solubility of more than about 0.1 wt % (weight percent) in an organic solvent. With a relatively high solubility in a common solvent, it is convenient to incorporate polymer (II) into devices through solution based processing techniques, which can be cost effective. Common solution based processes include spin coating, screen printing, stamp printing, dip coating, jet printing, and the like.

Polymer (II) may be used as semiconductors or charge transport materials in electronic devices such as organic photovoltaic cells, organic thin film field effect transistors (OFETs), or organic light emitting diodes (OLEDs), and the like.

Polymer (II) may also be used to form a p-channel TFT, photodiode, organic light emitting diode (OLED), sensor, or memory.

The polymer is of a p-type and, as noted above, can have bandgap below 1.9 eV. The polymer can be applied to form a low bandgap material in an electronic device, such as an OPV cell, in a solution-based deposition process. The resulting device can provide a relatively high PCE, such as from about 3.2 to about 5.4%.

PCE of an OPV device may be determined from measured short circuit current ($J_{sc}$), open circuit voltage ($V_{oc}$), and fill factor (FF), using the formula:

$$PCE = \frac{FF * V_{OC} * I_{SC}}{P_{light}},$$

where $P_{light}$ is the power intensity of irradiation light (at AM 1.5 global, 100 mW/cm$^2$), as described, for example, in Christoph Winder and Niyazi Serdar Sariciftci, "Low bandgap polymers for photon harvesting in bulk heterojunction solar cells," *J. Mater. Chem.*, 2004, vol. 14, pp. 1077-1086, the entire contents of which are incorporated herein by reference. Generally, $V_{oc}$ depends on the HOMO energy levels of the donors and LUMO energy levels of the acceptors in the active material, and $J_{sc}$ depends on the photon absorption of the active layer, and charge carriers generated at the donor-acceptor interface as well as charge collection efficiency at the electrodes. Thus, the low bandgap polymer described herein can provide increased photocurrent due to enhanced light absorption. A low bandgap polymer described herein can provide higher $V_{oc}$, higher $J_{sc}$, and also better FF, thus higher PCE.

FF depends on the charge dissociation, the charge carrier transport, and the recombination processes. When hole and electron transport are unbalanced, a build-up of space charge can result in a square root dependence of the photocurrent on voltage, resulting in low fill factors. The FF in materials formed of polymer (II) is relatively high. It is expected that this is due to the good charge mobility of the polymer and the ordered structure of the polymer. The polymer is expected to interact with acceptors to prevent substantial phase separation, thus facilitating formation of an interpenetrating network with the acceptors. The structural ordering in the polymer is expected to enhance transport properties, such as hole mobility.

Another embodiment relates to a method of forming an electronic device incorporating polymer (II). In an exemplary method, a layer of polymer (II) is formed by a solution-based process comprising spin coating, stamp printing, screen printing, or jet printing. The polymer layer or film may be formed on a substrate (not shown), which may be a plastic sheet formed of polyester, polycarbonate, or polyimide.

In one embodiment, a process for forming the device may include dissolving polymer (II) in a solution, applying the solution to a substrate, and drying the solution on the substrate to form a solid layer containing polymer (II).

A photovoltaic cell based on polymer (II) may include a layer formed of a mixture of polymer (II) and PCBM. This layer may be an active layer for the cell.

Polymer (II) may be conveniently mixed with PCBM to form bi-continuous phase with small domain size in order to achieve efficient charge separation between p-type materials and n-type materials, and good charge transportation through the resulting film. The weight ratio of polymer (II) to PCBM may vary from about 2:1 to 1:5.

Polymer (II) may be used in an organic semiconductor device.

In an exemplary process, a solution of polymer (II) may be deposited on a substrate. The solution may include a mixture of polymer (II) and an electron acceptor material, such as PCBM. An organic semiconductor layer is formed on the substrate with the solution.

The solution may be dried to form an active layer. The active layer may include a bicontinuous network structure with an average domain size less than about 100 nm. One of the phases is formed of polymer (II) and the other phase is formed of PCBM. The domain sizes may be less than 50 nm, such as from about 20 to about 30 nm, or even about 10 nm.

Without being limited to any particular theory, it is expected that polymer (II) can provide improved PCE due to the following reasons. Polymer (II) has both improved charge transport property and a morphology that permits good charge separation. The bandgap in polymer (II) is relative narrow/low, for example, in the range of about 1.3 to 1.9 eV, or from about 1.4 to about 1.7 eV. As both oligothiophene units and benzothiadiazole units are present and regularly arranged in polymer (II), the donor-acceptor structure results in a low bandgap. The selected oligothiophene block in polymer (II) and the selection and position of the side chains together ensure that the resulting polymer (II) has the desired charge transporting properties, and solubility and miscibility with PCBM to achieve the desired morphology.

In different embodiments, polymer (II) may be used in an active layer of the device. For example, when the device has both a n-type layer and a p-type layer, polymer (II) may be used to form the p-type layer (p-channel layer). The active layer may also be a mixture of a n-type material and polymer (II) (as the p-type material).

Exemplary embodiments of the present invention are further illustrated with the following examples, which are not intended to be limiting.

EXAMPLES

In the Examples, the starting materials were used as received, unless otherwise specified.

In the Examples, $^1$H and $^{13}$C NMR data were obtained using a Bruker™ DPX 400 MHz spectrometer with chemical shifts referenced to CDCl$_3$; matrix assisted laser desorption/ionization time-of-flight (MALDI-TOF) mass spectra were obtained on a Bruker Autoflex TOF/TOF instrument using dithranol as a matrix and silver trifluoroacetate as an ionizing salt when necessary; differential scanning calorimetry (DSC) was carried out under nitrogen on a DSC Q100 instrument (scanning rate of 10° C. min$^{-1}$); thermal gravimetric analysis (TGA) was carried out using TGA Q500 instrument (heating rate of 10° C. min$^{-1}$); cyclic voltammetry (CV) experiments were performed using an Autolab™ potentiostat (model PGSTAT30) by Echochimie™; and UV-Vis spectra were recorded on a Shimadzu™ model 2501-PC UV-VIS spectrometer.

CV measurements were made at room temperature in dichloromethane with 0.1 M tetrabutylammonium hexafluorophosphate as supporting electrolyte (scan rate of 100 mV.s$^{-1}$), using a three-electrode configuration with a platinum wire working electrode, a gold counter electrode, and a Ag/AgCl in 3 M KCl reference electrode. The measured potentials were converted to SCE (saturated calomel electrode) and the corresponding ionization potential (IP) and electron affinity (EA) values were derived from the onset redox potentials, based on −4.4 eV as the SCE energy level relative to vacuum (EA=$E_{red\text{-}onset}$+4.4 eV, IP=$E_{ox\text{-}onset}$+4.4 eV).

Example I

Synthesis of 3-(2-octyldodecyl)thiophene 1.3 g (54 mmol) of magnesium turnings, a catalytic amount of iodine, and 50 mL of dry THF was mixed in a flask and heated to slight reflux under nitrogen. A solution of 2-octyldodecyl bromide (18.1 g, 50 mmol) and 25 mL of dry THF was added drop-wise into the mixture. The mixture was then allowed to reflux for 3 h. After resulting grey solution was cooled to room temperature, transferred into a dry droping funnel, and added drop-wise into a dry THF solution of 3-bromothiophene (6.5 g, 40 mmol) and Ni(dppp)Cl$_2$ (160 mg, 1.2 mmol) at 0° C. The mixture was heated to reflux overnight under nitrogen atmosphere. The mixture was then cooled and a dilute hydrochloric acid aqueous solution was added to quench excess Grignard reagent. The crude product was extracted from the mixture with hexane, washed with water, and purified by silica gel chromatography eluting with hexane. The final product was 7.2 g of colorless oil (49%). The product was characterized by $^1$H NMR: (CDCl$_3$, 400 MHz, ppm) δ 7.23-7.21 (m, 1H), 6.90-6.88 (m, 2H), 2.56-2.55 (d, 2H, J=6.8 Hz), 1.61-1.59 (m, 1H), 1.25 (br, 32H), 0.90-0.87 (t, 6H).

Example II

Synthesis of 2-bromo-3-(2-octyldodecyl)thiophene

A solution of N-bromosuccinimide (2.58 g, 14.5 mmol) in 100 mL of dimethylformamide (DMF) was added drop-wise into a solution of 3-(2-octyldodecyl)thiophene (4.90 g, 13.2 mmol) in 300 DMF at −20° C. The mixture was stirred overnight at room temperature. Next, the DMF was removed under vacuum and 100 mL water was added. The mixture was extracted with hexane three times and the organic layers were collected. After removal of hexane, a crude product was obtained and was purified by column to afford 5.60 g of the final product in the form of colorless oil (96%). $^1$H NMR (CDCl$_3$, 400 MHz, ppm) δ 7.18-7.17 (d, 1H, J=5.6 Hz), 6.76-6.75 (d, 1H, J=5.6 Hz), 2.50-2.48 (d, 2H, J=7.2 Hz), 1.64 (m, 1H), 1.30-1.25 (br, 32H), 0.90-0.87 (t, 6H).

Example III

Synthesis of 5,5'-dibromo-4,4'-bis(2-octyldodecyl)-2,2'-bithiophene 2-bromo-3-(2-octyldodecyl)thiophene (5.32 g, 12 mmol), PdCl$_2$(PhCN)$_2$ (46.5 mg, 0.12 mmol), potassium fluoride (1.39 mg, 24 mmol), and dimethyl sulfoxide (DMSO) (60 mL). AgNO$_3$ (4.06 g, 24 mmol) was added to a 100 mL of Schlenk tube, in one portion. The resulting mixture was stirred at 120° C. for 3 h. Additional potassium fluoride (1.39 mg, 24 mmol) and AgNO$_3$ (4.06 g, 24 mmol) were then added to the mixture and the mixture was stirred for 8 h at 120° C. The reaction mixture was then cooled and passed through a Celite pad to remove black solids. The resulting cake was washed repeatedly with ethyl acetate. The filtrate was washed with water, dried over anhydrous magnesium sulfate, and concentrated under reduced pressure, resulting in a crude product. The crude product was purified by silica gel chromatography to produce 2.54 g of the final product, a light yellow oil (48%). $^1$H NMR (CDCl$_3$, 400 MHz, ppm) δ 6.73 (s, 2H), 2.46-2.44 (d, 4H, J=7.2 Hz), 1.64 (m, 2H), 1.25 (br, 64H), 0.89-0.86 (t, 12H). $^{13}$C NMR (CDCl$_3$, 100 MHz, ppm) δ 142.20, 136.03, 124.94, 108.50, 38.51, 34.27, 33.39, 31.93, 31.91, 29.97, 29.67, 29.64, 29.63, 29.59, 29.34, 29.32, 26.53, 22.68, 22.67, 14.08.

Example IV

Synthesis of 3',4"-bis(2-octyldodecyl)-2,2':5',2":5",2"'-quaterthiophene

A 20 mL microwave vial was charged with 2-(tributylstannyl)thiophene (1.03 g, 2.77 mmol), 5,5'-dibromo-4,4'-bis(2-octyldodecyl)-2,2'-bithiophene (1.11 g, 1.26 mmol), Pd(PPh$_3$)$_4$ (160 mg, 0.14 mmol), and DMF 15 mL. The vial was heated in a microwave reactor for 20 min at 180° C. After the reaction was finished, the mixture was poured into water and the mixture was extracted 3 times. The combined organic fractions were washed sequentially with water, brine, and then dried over sodium sulfate. After solvent removal, the residue was purified by silica gel chromatography with hexane as an eluent to produce 0.84 g of the final product (yellow oil, 75%). $^1$H NMR (CDCl$_3$, 400 MHz, ppm) δ 7.31-7.30 (d, 2H, J=5.2 Hz), 7.12-1.11 (m, 2H), 7.07-7.04 (m, 2H), 6.95 (s, 2H), 2.67-2.65 (d, 4H, J=7.2 Hz), 1.69 (m, 2H), 1.24 (br, 64H), 0.89-0.86 (t, 12H).

Example V

Synthesis of 5,5'''-dibromo-3',4"-bis(2-octyldodecyl)-2,2':5',2":5",2"'-quaterthiophene A solution of N-bromosuccinimide (351 mg, 1.97 mmol) in 30 mL of DMF was added drop-wise into a solution of 3',4"-bis(2-octyldodecyl)-2,2':5',2":5",2"'-quaterthiophene (840 mg, 0.94 mmol) in DMF (150 mL) and chloroform (30 mL) at −20° C. The mixture was stirred overnight at room temperature. The DMF was removed under vacuum and 100 mL water was added to the mixture. The mixture was extracted 3 times with hexane and the combined organic layers were dried over anhydrous MgSO$_4$. After removal of hexane, the crude product was purified by silica gel column chromatography to afford 986 mg of a final product (yellow oil, 98%). $^1$H NMR (CDCl$_3$, 400 MHz, ppm) δ 7.01-7.00 (d, 2H, J=3.6 Hz), 6.93 (s, 2H), 6.86-6.85 (d, 2H, J=3.6 Hz), 2.62-2.60 (d, 4H, J=7.2 Hz), 1.66 (br, 2H), 1.24 (br, 64H), 0.88-0.86 (t, 12H). $^{13}$C NMR (CDCl$_3$, 100 MHz, ppm) δ 140.62, 137.43, 135.14, 130.31, 129.08, 126.95, 126.64, 111.87, 38.83, 38.81, 33.43, 31.90, 29.94, 29.93, 29.64, 29.63, 29.60, 29.56, 29.33, 29.30, 26.41, 22.66, 22.65, 13.82.

Example VI

Synthesis of poly((3',4"-bis(2-octyldodecyl)-2,2':5',2":5",2"'-quaterthiophene-2,2"'-diyl)-(dithieno[3,2-b;2',3'-d]thiophene-2,6-diyl)) (PQTDTT)

2,6-bis-trimethylstannanyl-dithieno[3,2-b;2',3'-d]thiophene (96 mg, 0.184 mmol, 1 equivalent), 5,5"'-dibromo- 3',4"-di(2-octyldodecyl)-[2,2';5',2";5",2"']quaterthiophene (193 mg, 0.184 mmol, 1 equivalent), tri(o-toyl)phosphine (4.5 mg, 14.7 μmol, 8 mol % equivalent), tris(dibenzylidene-acetone)dipalladium (3.4 mg, 3.68 μmol % equivalent) and dry chlorobenzene (20 ml) were added to a Schlenk flask under nitrogen. The flask was securely sealed and stirred for 72 h at 120° C. After cooling to room temperature, the reaction mixture was precipitated into a mixture of methanol (200 ml) and concentrated hydrochloric acid (15 ml) and the mixture was stirred for 16 hrs. The precipitate was collected and Soxhlet extracted sequentially with ethanol, hexane and chloroform for 48 hrs each. The remaining solid was dissolved in chlorobenzene and precipitated into a methanol solution. The collected solid was dried under vacuum. The bulk product yield by this procedure was 40%.

Figure 8:
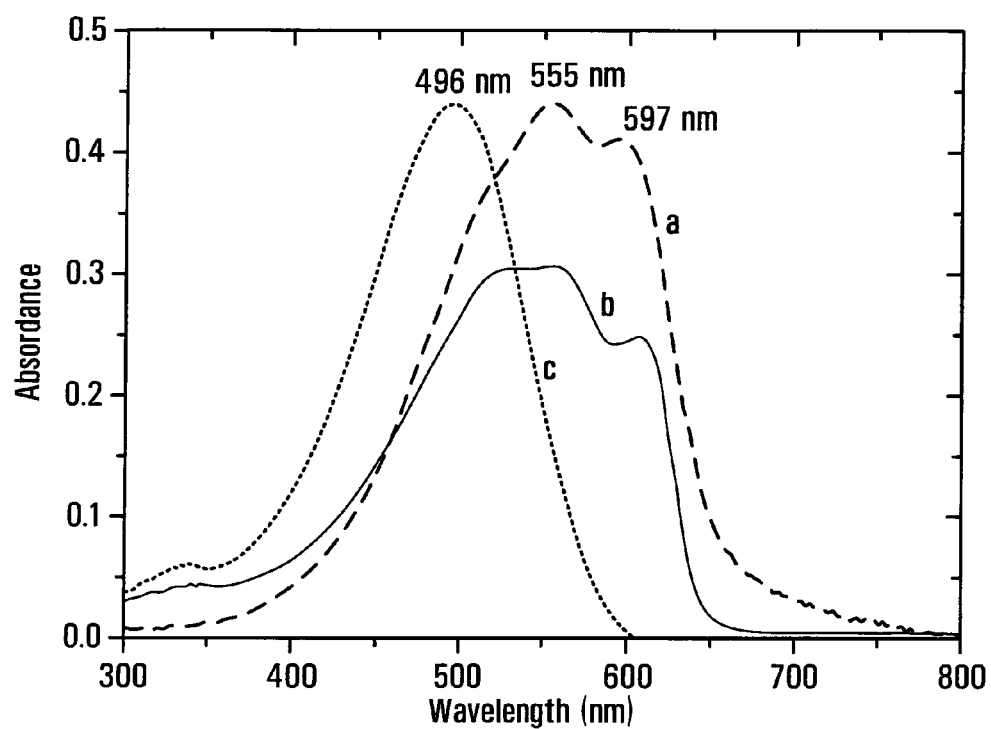
FIG. 8 is a line diagram showing UV-vis absorption spectra of sample polymers.

FIG. 8 shows representative UV-vis spectra of sample PQTDTT polymers produced. In FIG. 8, line (a) represents data measured from a cast thin film formed from sample PQTDTT; line (b) represents data measured at room temperature from sample PQTDTT in a dilute solution with chlorobenzene as the solvent; and line (c) represents data measured from the dilute solution of line (b) but at 60° C.

TGA measurement showed that a 5% weight loss of the sample polymer took place at 370° C. DSC measurement showed a melting point temperature at 234° C. The high decomposition temperature of the material indicates good thermal stability and the high melting point indicates good morphological stability for film samples.

The sample polymer was also subject to cyclic voltammetric measurement by using a platinum disk as working electrode and a silver wire as reference electrode. Ferrocene was used for potential calibration (Fc+/Fc: 0.5V). The test results showed an oxidative potential of 0.85V (onset), corresponding to HOMO level of −5.15 eV.

Example VII

Sample OFETs (OTFTs) as shown in FIG. 4 were fabricated as described above. The substrates for the gate layer were n+-Si or p+Si with 200 nm of SiO$_2$ (gate dielectric) on top. The organic thin film (35-40 nm) was grown on top of SiO$_2$ by a spin coating technique. About 100 nm thick Au layer was deposited on the thin film using a shadow mask to form source and drain contacts.

The substrates (wafers) were subject to routine cleaning using ultrasonication in acetone, methanol and de-ionized water. Cleaned wafers were dried under flow of nitrogen and heated at 100° C. for 5 minutes.

The cleaned and dried p+-Si (or n+-Si)/SiO$_2$ wafers were subject to UV-ozone treatment for 20 minutes. In order to improve organization of organic molecules on p+-Si (or n+-Si)/SiO$_2$ substrates, several of the substrates were subject to SAM treatment before use.

Octyltricholorosilane (OTS) SAM treatment were performed as follows. The p+-Si (or n+-Si)/SiO$_2$ substrates were kept in desiccator with few drops of OTS. The dessicator was subjected to vacuum for 3 minutes and then placed in an oven at 110° C. for three hours. The p+-Si (or n+-Si)/SiO$_2$ substrates were next removed from the desiccator, and thoroughly rinsed with isopropanol and dried under flow of nitrogen gas.

Thin film of PQTDTT was grown on the treated substrate by spin coating using 8 mg/ml solution of PQTDTT in chlorobenzene. The coated thin films were annealed at an elevated temperature. The annealing temperature was varied at 80, 120, 160, or 200° C. respectively, to study the effect of annealing on device performance.

Once organic thin films were grown on substrates, top contact bottom gate OTFTs as schematically shown in FIG. 4 were fabricated by depositing ~100 nm of gold as source and drain contacts using shadow masks. The typical OTFT devices had 50, 100 or 200 μm channel length (L) in combination to 1 mm or 3 mm channel width (W).

Figure 9:
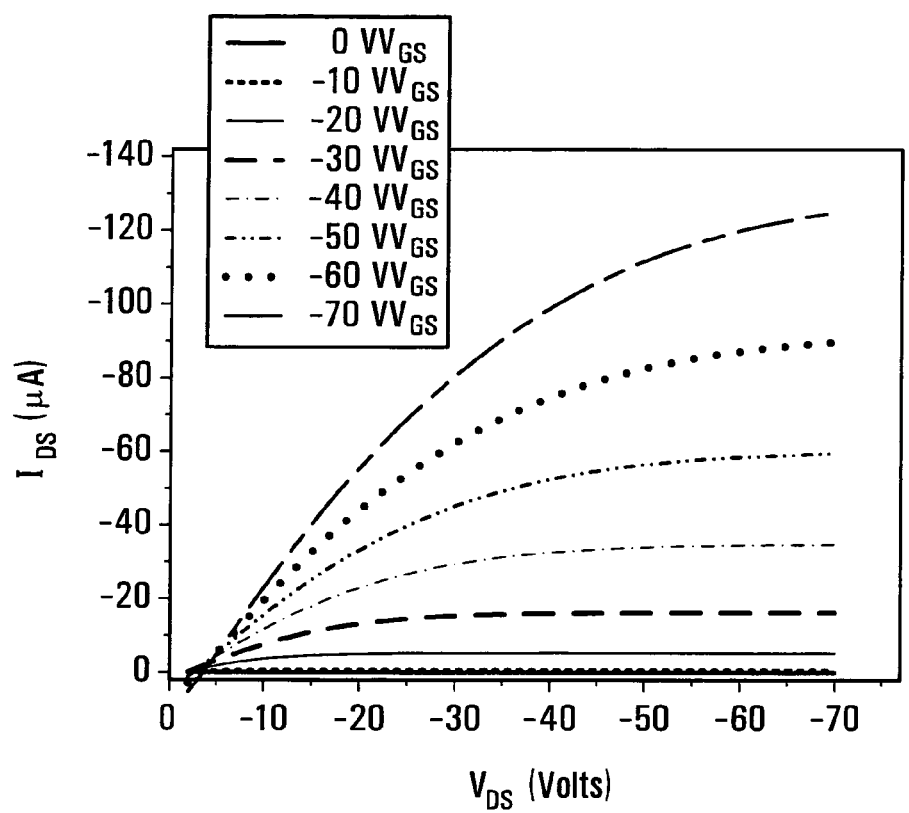
FIG. 9 is a line graph showing $V_d$-$I_d$ relationships measured from a sample OFET as shown in FIG. 4.
Figure 10:
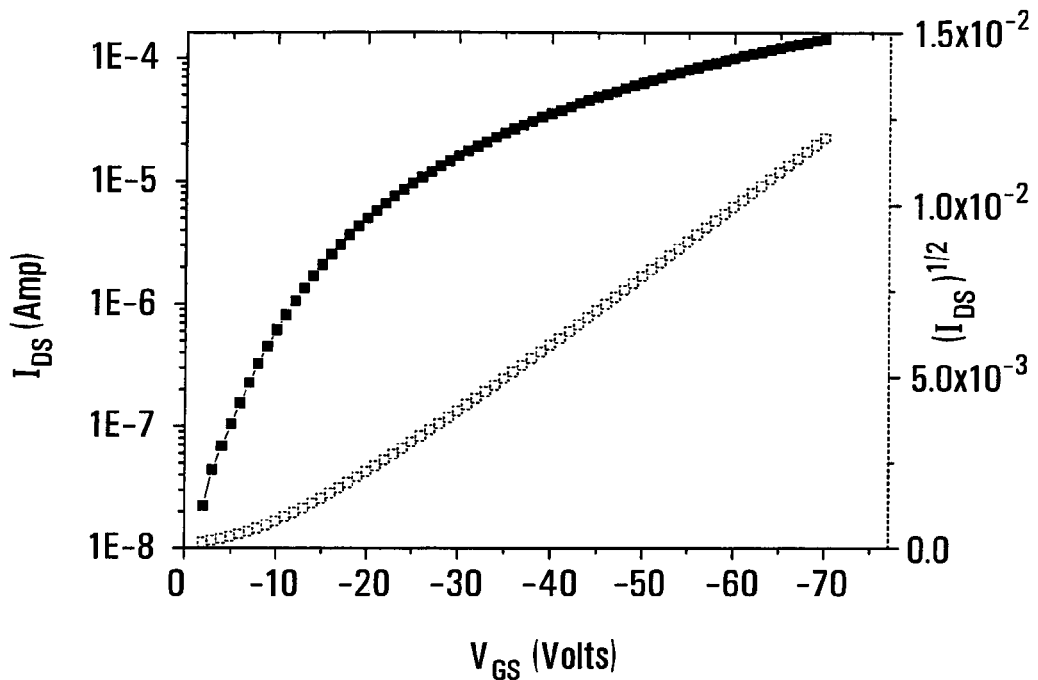
FIG. 10 is a line graph showing $V_g$-$I_d$ relationships measured from the sample OFET as shown in FIG. 4.

The fabricated sample OTFTs were characterized in glove box under nitrogen using Keithley 4200™ parameter analyzer. Representative $V_{DS}$-$I_{DS}$ and $V_{GS}$-$I_{DS}$ characteristic of the sample OTFTs, with PQTDTT as the organic active (channel) layer on OTS treated p+-Si/SiO$_2$ substrates having L/W (100/1000), are shown in FIGS. 9 and 10 respectively. The results of FIG. 10 were obtained with $V_{ds}$=−60V. The sample OTFT for FIGS. 9 and 10 had a semiconductor channel layer formed from a thin film of PQTDTT, where the PQTDTT semiconductor thin film was pre-annealed at 200° C. FIG. 9 shows data measured at different gate voltages as listed in the legend.

As can be seen, the sample OTFTs showed V-I characteristics typical of p-channel materials. It was also found that sample OTFTs exhibited hole mobility of 0.14 cm$^2$/V-sec ($V_{TH}$: −14.0 Volts, $I_{ON}$/$I_{OFF}$: ~10$^4$) for sample devices with non-annealed PQTDTT thin film, or up to 0.44 cm$^2$/V-sec ($V_{TH}$: ~10.6 Volts, $I_{ON}$/$I_{OFF}$: ~10$^4$) for sample devices with PQDTDTT thin film pre-annealed at 200° C. The effect of annealing on device performance is summarized in Table I, wherein samples 1 to 4 were formed of the same materials but were subjected to different annealing temperatures.

The TFT devices were then characterized using a Keithley SCS-4200 probe station under an ambient environment in dark. The FET mobility was calculated using the following equation in the saturation regime from the gate sweep:

$$I_{SD}=\mu C_i(V_G-V_T)^2(W/2L)$$

where $I_{SD}$ is the drain current, μ is the field-effect mobility, $C_i$ is the capacitance per unit area of the gate dielectric layer (SiO$_2$, 200 nm, Ci=17.25 nF/cm$^2$), and $V_G$ and $V_T$ are respectively gate voltage and threshold voltage. $V_T$ was derived from the relationship between the square root of $I_{SD}$ at the saturated regime and $V_G$ by extrapolating the measured data to $I_{SD}$=0. W and L are respectively channel width and length. $I_{on}$/$I_{off}$ is the ratio of the saturation source-drain current when the gate voltage $V_G$ is equal to or greater than the drain voltage $V_D$ to the source-drain current when the gate voltage $V_G$ is zero.

The TFT device fabricated at room temperature showed high mobility of 0.14 cm$^2$/Vs. The devices with pre-annealing demonstrated higher mobility, e.g, at 200° C., and the mobility increased to 0.44 cm$^2$/Vs. The increased mobility of TFT devices with pre-annealing was expected to be due to improved packing of the polymer chains after thermal annealing.

TABLE I

OTFT performance of PQTDTT

| Sample | Annealing Temperature (° C.) | Charge Mobility, μ$_h$ (cm$^2$/Vs) | $V_{TH}$ (Volts) | $I_{ON}$/$I_{OFF}$ |
|---|---|---|---|---|
| 1 | 25 | 0.14 | 14.0 | 10$^4$ |
| 2 | 100 | 0.17 | 14.0 | 10$^4$ |
| 3 | 150 | 0.23 | 15.2 | 10$^4$ |
| 4 | 200 | 0.44 | 10.6 | 10$^4$ |

Example VIII

Synthesis of 2,1,3-Benzothiadiazole-4,7-bis(boronic acid pinacol ester)

A mixture of 4,7-dibromo-2,1,3-benzothiadiazole (2.94 g, 10 mmol), bis(pinacolato)diboron (5.59 g, 22 mmol), PdCl$_2$ (dppf) (490 mg, 0.6 mmol), and KOAc (2.95 g, 30 mmol) in degassed 1,4-dioxane (30 mL) was stirred at 80° C. for 6 h. The cooled mixture was quenched with water and extracted with ethyl acetate. The organic layers were collected, washed with brine and dried over sodium sulfate. The solvent was removed and the residue was purified by silica gel column chromatography eluting with gradient hexane/ethyl acetate to produce the final product, which was a khaki powder (1.71 g, 44%). $^1$H NMR (CDCl$_3$, 400 MHz, ppm) δ 8.13 (s, 2H), 1.44 (s, 24H).

Example IX

Synthesis of 4,7-bis(2-trimethylstannylthien-5-yl)-2,1,3-benzothiadiazole

A mechanically stirred solution of 2,2,6,6-tetramethylpiperidine (TMP) (0.55 g, 4 mmol) in dry THF (25 mL) under argon was cooled to −78° C. Next, n-butyllithium (3.9 mmol) was rapidly added to the solution. The resulting solution was allowed to warm to room temperature. It was kept at room temperature for 10 min and subsequently cooled to −78° C. again. A solution of 4,7-bis(2-thienyl)-2,1,3-benzothiadiazole in 5 mL of dry THF was then added drop-wise to the cooled solution. The resulting solution has a deep purple color and was stirred at −78° C. for 30 min. A 1M solution of trimethyltin chloride in hexanes (3.9 mL) was then added. The reaction mixture was allowed to warm to room temperature and stirred overnight. Water was added to quench the reaction. Diethyl ether was added, and the mixture was washed 3 times with 0.1M HCl to remove the TMP. The solution was then dried with MgSO$_4$. The solvent was removed, and the final product (0.42 g, 45%) was re-crystallized in ethanol to yield orange needles. $^1$H NMR (CDCl$_3$): 8.19 (d, 2H), 7.88 (s, 2H), 7.30 (d, 2H), 0.44 (s, 18H). $^{13}$C NMR (CDCl$_3$): 152.7, 145.1, 140.2, 136.1, 128.4, 125.9, 125.8, −8.2.

Example X

Synthesis of Sample polymer II-P1a

Synthesis Route 1 of FIG. 6 was followed in this Example.
A 25 mL round bottom flask was charged with 5,5'''-dibromo-3',4''-bis(2-octyldodecyl)-2,2':5',2'':5'',2'''-quaterthiophene (from Example V) (398.7 mg, 0.38 mmol), 2,1,3-benzothiadiazole-4,7-bis(boronic acid pinacol ester) (147.5 mg, 0.38 mmol), and Aliquate 336™ (20 mg, 0.05 mmol). Pd(PPh$_3$)$_4$ (2 mg) was added to the flask in a glove-box. Degassed toluene (1.45 mL) and 2 M K$_2$CO$_3$ aqueous solution (0.72 mL) were added into the mixture in the flask by syringe. After heating the mixture at 83° C. under nitrogen atmosphere for 48 h, excess phenylboronic acid and bromobenzene were added sequentially with a 12-hour interval, as end-capping reagents. The mixture was extracted with chloroform for three times. The collected organic extracts were washed with water and brine, and then dried over sodium sulfate. The salt was filtered off from the dry mixture and the filtrate was concentrated into a small volume. The polymer solution was added drop-wise into stirred methanol. After filtration, the collected solid was purified by Soxhlet extraction with methanol and hexane sequentially. The product was then dried under vacuum to produce 318 mg of Sample polymer II-P1a (82%).

The product was characterized and was found to have the following properties: Mn=16000; Mw=38000; PDI=2.37; $^1$H NMR (CDCl$_3$, 400 MHz, ppm) 8.13 (s, 2H), 7.87 (s, 2H), 7.52 (2H), 7.03-6.99 (m, 2H), 2.79 (br, 4H), 1.79 (br, 2H), 1.32-1.22 (m, 64H), 0.85-0.83 (m, 12H).

The bandgap value for II-P1a was found to be about 1.59 eV.

Figure 11:
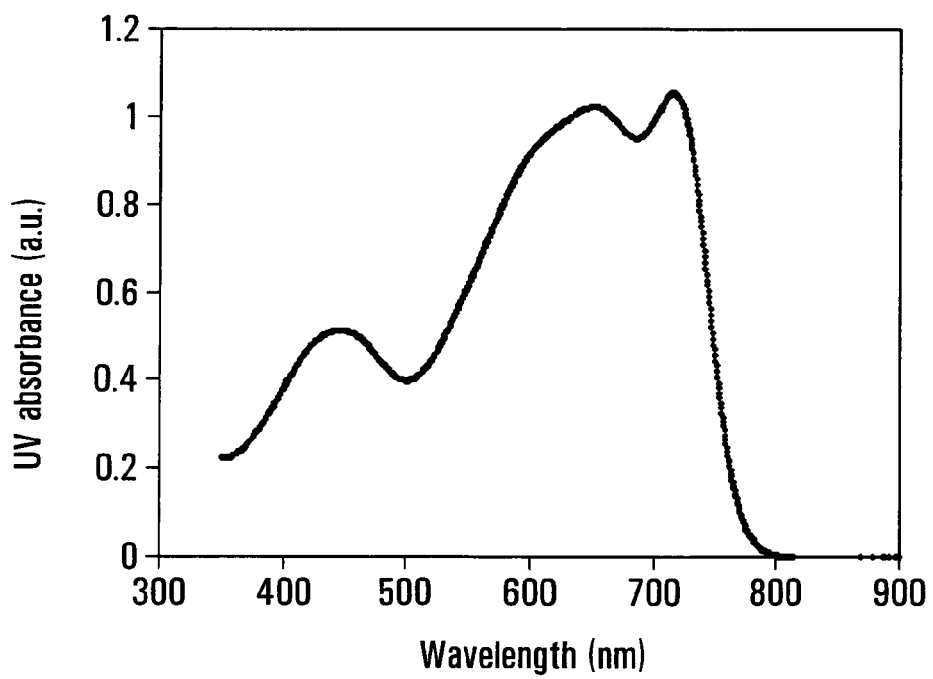
FIG. 11 is a line graph showing UV-vis absorption spectrum of a sample polymer in chlorobenzene.

The UV-vis absorption spectra of a sample polymer II-P1a in chlorobenzene were measured. A representative spectrum is shown in FIG. 11. As can be seen, the absorbance was from about 400 nm to about 760 nm, and maximized (referred to as UV max herein) at about 730 nm.

Example XI

Synthesis of Sample polymer II-P1b

Synthesis Route 2 of FIG. 6 was followed in this Example.
4,7-bis(2-trimethylstannylthien-5-yl)-2,1,3-benzothiadiazole (183.2 mg, 0.29 mmol), 5,5'-dibromo-4,4'-di(2-octyldodecyl)-2,2'-bithiophene (259 mg, 0.29 mmol), tris(dibenzylideneacetone)dipalladium(0) (10.71 mg, 4 mol %), and tri(o-tolyl)phosphine (14.25 mg, 16 mol %) were added to a 100 mL vial equipped with a mechanical stirrer. The vial was purged with argon and then sealed. Chlorobenzene (20 mL) was added through a septum and the reaction mixture was then heated at 120° C. for 72 h using an oil bath. The reaction mixture was then poured into 200 mL of methanol and 10 mL of HCl. The polymer was filtered and subjected to sequential Soxhlet extractions with methanol (24 h), hexanes (24 h), acetone (12 h), chloroform (24 h) and chlorobenzene (24 h). The chlorobenzene fraction was concentrated and precipitated into 200 mL of methanol. The crude product was purified by filtration to obtain a purified polymer product (118 mg, 39%); which was a black solid.

The product was characterized and was found to have the following properties: $M_n/M_w$=62 k/174 k; Td=405° C.; UV max in chloroform=716 nm; bandgap=1.59 eV; HOMO/LUMO=−5.23/−3.64 eV:

Example XII

Synthesis of Sample polymer II-P3

The synthesis route used in this Example is illustrated in FIG. 7. The procedure in Example X for preparing Sample polymer II-P1b was followed to prepare polymer II-P3, with the change that 5,5'-dibromo-4,4'-di(2-octyldodecyl)-2,2'-bithiophene was replaced with 5,5'''-dibromo-3',4''-di(2-octyldodecyl)-2,2':5',2'':5'',2'''-quaterthiophene (190 mg, 0.181 mmol), and the amount of input 4,7-bis(2-trimethylstannylthien-5-yl)-2,1,3-benzothiadiazole was reduced to 113.3 mg (0.181 mmol). The resulting black solid product was polymer II-P3 (178 mg, 83%).

The product was characterized and was found to have the following properties: Td=351° C.; UV max in chloroform=626 nm; bandgap=1.67 eV; HOMO/LUMO=−5.21/−3.54 eV.

Example XIII

Sample OPV Devices

Sample polymer II-P1a or II-P1b was mixed with PCBM to fabricate OPV cells and devices photovoltaic. The respective sample polymer and PCBM were dissolved in dichlorobenzene (weight ratio=1:1, 1:2, 1:4) at a polymer concentration of 10 mg/ml. Patterned indium tin oxide (ITO)-coated glass were used as substrates (with 160 nm of ITO and an average sheet resistance of 14 Ω/square. The ITO/glass substrates were cleaned in detergent (30 min), distilled water (10 min, 2 times), acetone (15 mins) and isopropanol (20 min). The substrates were then baked at 60° C. to remove residual solvents. The dried substrates were subjected to oxygen plasma cleaning for 10 min prior to spin coating a 40 nm of poly(3, 4-ethylenedioxythiophene)poly(styrenesulfonate) (PEDOT:PSS) hole transporting layer, followed by baking at 120° C. for 10 min. Subsequently, sample compositions containing polymer:PCBM blends were spun coat on top of the PEDOT:PSS layer with a spinning speed of 500 rpm for 120 seconds in inert gas glove box. The metal cathode layer (Ca/Ag) was next evaporated through a shadow mask at a pressure of 8×10$^{-5}$ Pa to obtain devices with an active area of 9 mm$^2$. The organic solar cells were characterized under simulated AM1.5G solar irradiation with a power intensity of 100 mW/cm$^2$.

Figure 12:
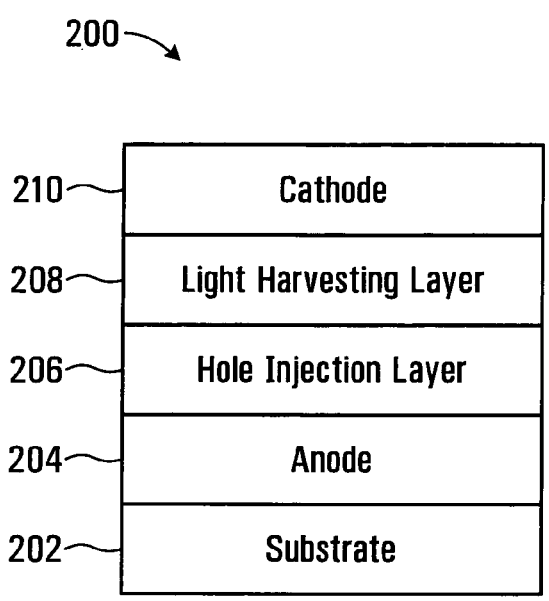
FIG. 12 is a cross-sectional elevation view of a sample organic photovoltaic (OPV) cell, exemplary of an embodiment of the present invention.

The structure of a sample OPV device 200 is schematically illustrated in FIG. 12, exemplary of an embodiment of the present invention. Device 200 had a multi-layer structure including a substrate layer 202 (it can be rigid substrate such as glass, or flexible substrate such as PET, PEN), an anode layer 204 (it can be ITO or other anode materials) on substrate layer 202, a hole-injection layer 206 (for example, PEDOT:PSS or MoO$_3$) on anode layer 204, a light harvesting layer 208 (here is the blend of the disclosed polymer and PCBM) on top of layer 206, and a cathode layer 210 (it can be Ca/Ag, Al, LiF/Al, CsCO$_3$/Al etc) on top of layer 208. Layers 202, 204, 206, and 210 were constructed and made of materials as in conventional OPV devices. Layer 208 was formed of a sample polymer or polymer film described herein.

Figure 13:
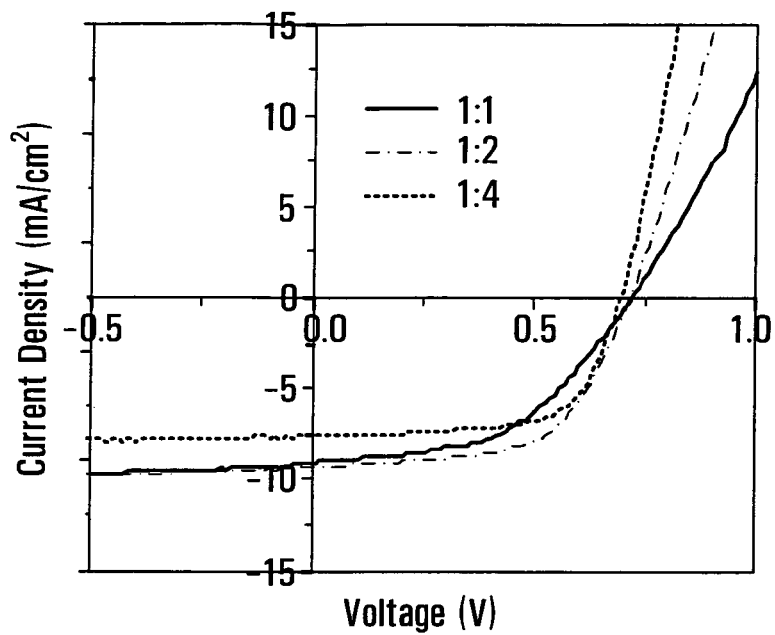
FIGS. 13, 14, 15 are line graphs showing representative measured I-V curves of sample organic photovoltaic (OPV) cells containing sample polymers shown in FIG. 5 as the active material.
Figure 14:
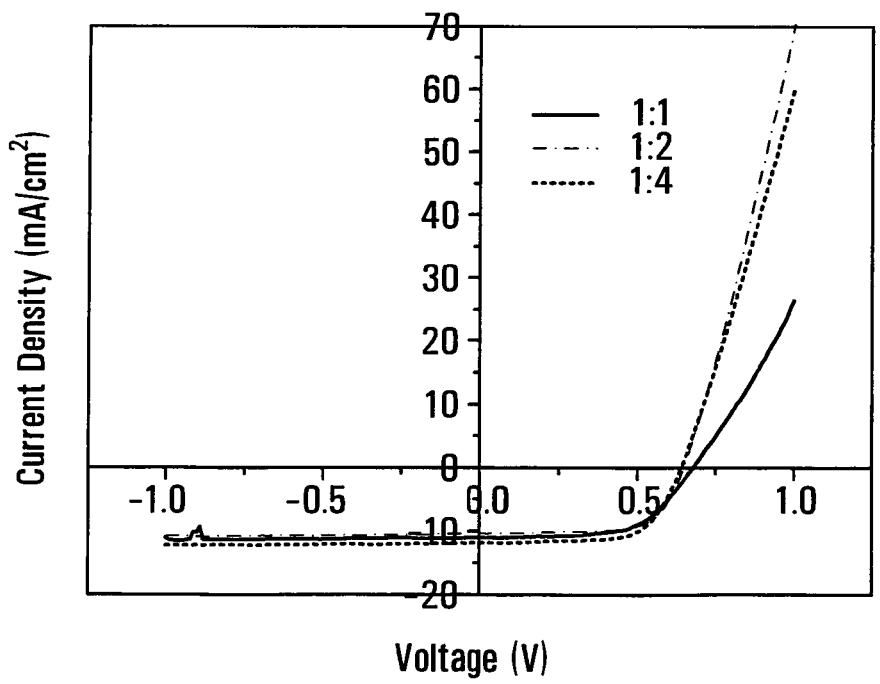
Figure 15:
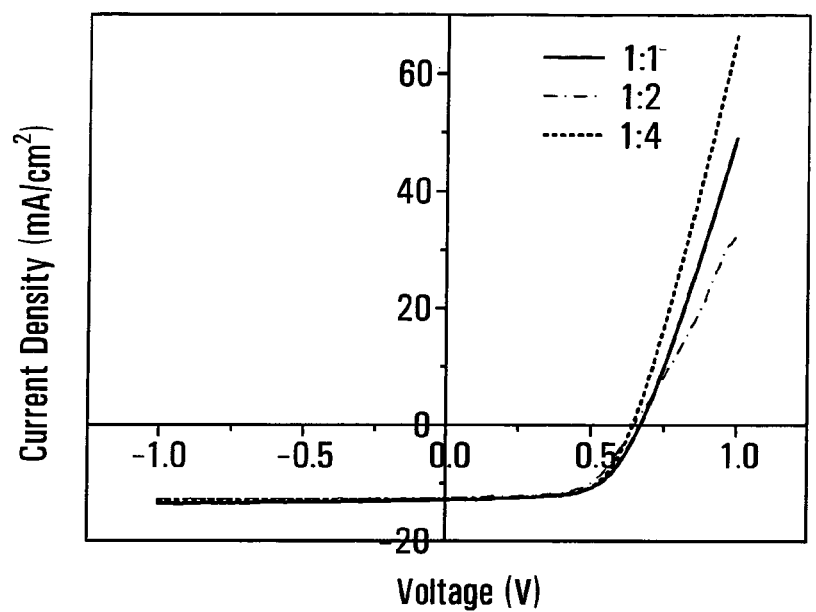

Representative test results are shown in FIG. 13 (for polymer II-P1a and PC60BM), FIG. 14 (for polymer II-P1b and PC60BM) and FIG. 15 (for polymer II-P1b and PC70BM), where PC$_{60}$BM is [6,6]-phenyl C$_{61}$-butyric acid methyl ester and PC$_{70}$BM is [6,6]-phenyl C$_{71}$-butyric acid methyl ester. The ratio listed in the legend indicates the weight ratio of polymer to PCBM in the active layer. Some measured and calculated performance values of the sample devices with different active layer compositions are listed in Table II.

Figure 16:
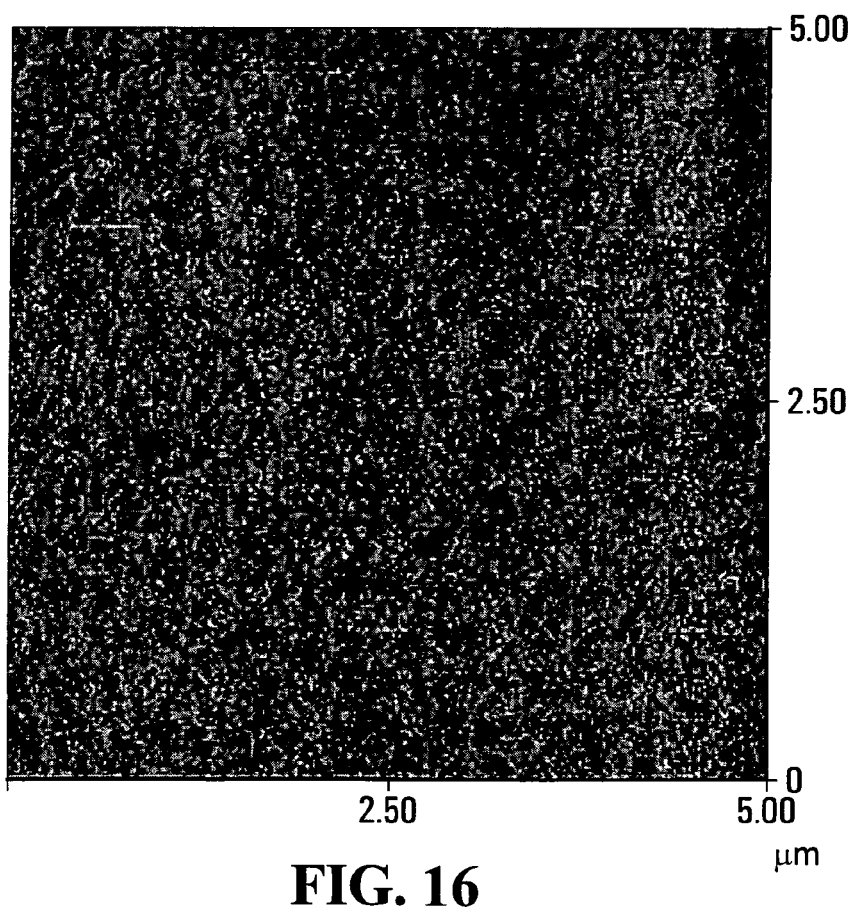
FIG. 16 is an atomic force microscopy (AFM) image of a sample film containing a sample polymer shown in FIG. 5.

FIG. 16 shows an AFM image of a sample film formed of sample polymer II-1b and PC60BM film with a weight ratio of: 1:4.

TABLE II

| Sample Device | Polymer | PCBM | Polymer/PCBM (weight ratio) | $J_{sc}$ (mA/cm$^2$) | $V_{oc}$ (V) | FF (%) | PCE (%) |
|---|---|---|---|---|---|---|---|
| 1 | II-P1a | PC60BM | 1:1 | 9.09 | 0.72 | 49.2 | 3.21 |
|   |       |        | 1:2 | 9.29 | 0.72 | 59.3 | 3.94 |
|   |       |        | 1:4 | 7.55 | 0.69 | 66.3 | 3.48 |
| 2 | II-P1b | PC60BM | 1:1 | 11.0 | 0.68 | 60.6 | 4.51 |
|   |       |        | 1:2 | 10.4 | 0.65 | 69.1 | 4.65 |
|   |       |        | 1:4 | 11.7 | 0.64 | 67.1 | 5.03 |
| 3 | II-P1b | PC70BM | 1:1 | 12.9 | 0.67 | 63.0 | 5.42 |
|   |       |        | 1:2 | 12.5 | 0.65 | 62.8 | 5.07 |
|   |       |        | 1:4 | 12.7 | 0.64 | 66.0 | 5.39 |

As can be seen, the PCE of the sample devices varied from about 3.21 to about 5.42%.

When a list of items is given herein with an "or" before the last item, any of the listed items or any suitable combination of the listed items may be selected and used. For any list of possible elements or features provided in this specification, any sublist falling within a given list is also intended. Similarly, for any range provided, any subrange falling within a given range is also intended.

Of course, the above described embodiments are intended to be illustrative only and in no way limiting. The described embodiments are susceptible to many modifications of form, arrangement of parts, details and order of operation. The invention, rather, is intended to encompass all such modification within its scope, as defined by the claims.

What is claimed is:

1. A polymer comprising a polymeric chain represented by

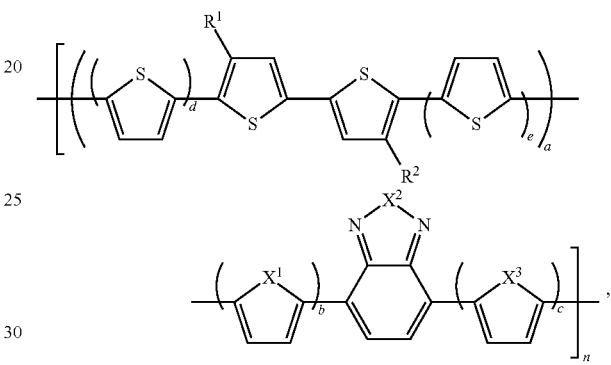

wherein
  a, b, c, d, e, and n are integers, a from 1 to 3, each of b and c being independently 0 or 1, each of d and e being independently 1 or 2, and n from 2 to 5000;
  R$^1$ is a first side chain except —COOalkyl;
  R$^2$ is a second side chain except —COOalkyl; and
  each of X$^1$, X$^2$ and X$^3$ is independently O, S, or Se.

2. The polymer of claim 1, wherein at least one of said side chains has from 6 to 30 backbone atoms.

3. The polymer of claim 1, having a number average molecular weight (M$_n$) of from 2,000 to 1,000,000 g/mol.

4. The polymer of claim 1, wherein n is from 5 to 1,000.

5. The polymer of claim 1, wherein at least one of said side chains comprises alkyl, siloxy, alkenyl, alkynyl, amine, ether, carbonyl, amide, sulfonyl, or sulfinyl.

6. The polymer of claim 5, wherein said alkyl has from 1 to 30 carbon atoms.

7. The polymer of claim 1, wherein each of X$^1$, X$^2$, and X$^3$ is S.

8. A device comprising a polymer comprising a polymeric chain represented by

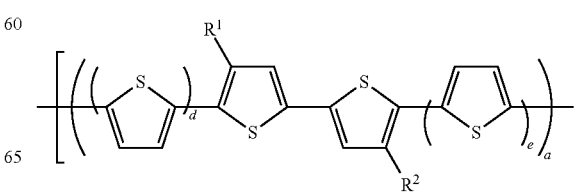

-continued

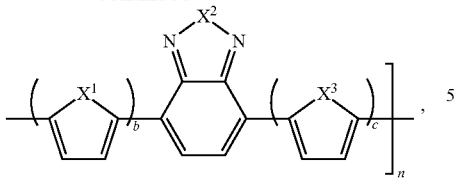

wherein
a, b, c, d, e, and n are integers, a from 1 to 3, each of b and c being independently 0 or 1, each of d and e being independently 1 or 2, and n from 2 to 5000;
$R^1$ is a first side chain except —COOalkyl;
$R^2$ is a second side chain except —COOalkyl; and
each of $X^1$, $X^2$ and $X^3$ is independently O, S, or Se.

9. A method for forming an electronic device comprising a semiconductor comprising a polymer comprising a polymeric chain represented by

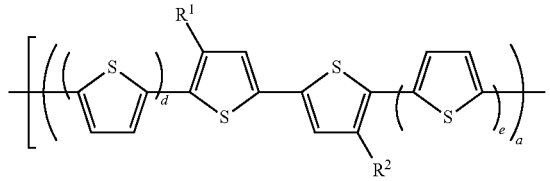

-continued

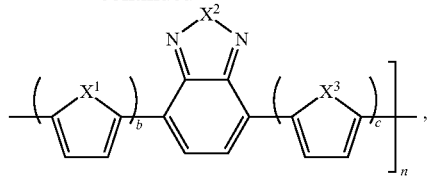

wherein
a, b, c, d, e, and n are integers, a from 1 to 3, each of b and c being independently 0 or 1, each of d and e being independently 1 or 2, and n from 2 to 5000;
$R^1$ is a first side chain except —COOalkyl;
$R^2$ is a second side chain except —COOalkyl; and
each of $X^1$, $X^2$ and $X^3$ is independently O, S, or Se, the method comprising:
dissolving said polymer in a solution;
applying said solution comprising said polymer to a substrate; and
drying said solution to form a solid layer comprising said polymer on said substrate.

* * * * *